(12) United States Patent
Hollander

(10) Patent No.: US 12,188,065 B2
(45) Date of Patent: Jan. 7, 2025

(54) PEPTIDES AND CONJUGATES

(71) Applicant: THE UNIVERSITY OF LIVERPOOL, Liverpool Merseyside (GB)

(72) Inventor: Anthony Hollander, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 930 days.

(21) Appl. No.: 17/042,682

(22) PCT Filed: Mar. 29, 2019

(86) PCT No.: PCT/GB2019/050917
§ 371 (c)(1),
(2) Date: Sep. 28, 2020

(87) PCT Pub. No.: WO2019/186190
PCT Pub. Date: Oct. 3, 2019

(65) Prior Publication Data
US 2021/0123036 A1 Apr. 29, 2021

(30) Foreign Application Priority Data

Mar. 29, 2018 (GB) .................................... 1805306
Oct. 26, 2018 (GB) .................................... 1817486

(51) Int. Cl.
*C12N 9/64* (2006.01)
*A61K 47/50* (2017.01)
*C07K 14/47* (2006.01)

(52) U.S. Cl.
CPC ............ *C12N 9/6491* (2013.01); *A61K 47/50* (2017.08); *C07K 14/47* (2013.01); *C12Y 304/24024* (2013.01)

(58) Field of Classification Search
None
See application file for complete search history.

(56) References Cited

U.S. PATENT DOCUMENTS 6,184,021 B1 2/2001 Senior
10,000,554 B2 * 6/2018 Sekiguchi ............. A61L 27/227

FOREIGN PATENT DOCUMENTS

| GB | 2468757 A | 9/2010 | |
| WO | WO-2007144781 A2 * | 12/2007 | ............. C07K 14/78 |
| WO | 2003/002729 A1 | 1/2009 | |
| WO | 2012112690 A2 | 8/2012 | |
| WO | 2017210598 A1 | 12/2017 | |
| WO | 2019/186190 A1 | 10/2019 | |

OTHER PUBLICATIONS

Obermaier, C., Griebel, A., Westermeier, R. (2015). Principles of Protein Labeling Techniques. In: Posch, A. (eds) Proteomic Profiling. Methods in Molecular Biology, vol. 1295. Humana Press, New York, NY. doi.org/10.1007/978-1-4939-2550-6_13 (Year: 2015).*
Xu et al., "Contributions of the MMP-2 collagen binding domain to gelatin cleavage substrate binding via the collagen binding domain is required for hydrolysis of gelatin but not short peptides", Matrix Biology 23: 171-181. (Year: 2004).*
Xu et al., NMR Mapping and Functional Confirmation of the Collagen Binding Sites of MMP-2, Biochemistry, 2009, vol. 48(25), pp. 1-21.
Trexler et al., Peptide Ligands for the FN2 Modules of Matrix Metalloproteinase 2 (MMP-2), , Journal of Cell Biology, 2002.
Briknarova et al., The second type II module from human matrix metalloproteinase 2: structure, function and dynamics, Structure, 1999, vol. 7(10), pp. 1235-1245.
Gehrmann et al., Modular Autonomy, Ligand Specificity, and Functional Cooperativity of the Three In-tandem Fibronectin Type II Repeats from Human Matrix Metalloproteinase 2, The Journal of Biological Chemistry, 2004, vol. 279(5), pp. 46921-46929.
Gehrmann et al., The Col-1 Module of Human Matrix Metalloproteinase-2 (MMP-2): Structural/Functional Relatedness between Gelatin-Binding Fibronectin Type II Modules and Lysine-Binding Kringle Domains, Biol. Chem., 2002, vol. 383, pp. 137-148.
GB Search Report for GB1805306.6 dated Nov. 28, 2018, 2 pages.
Xu et al., Functional basis for the overlap in ligand interactions and substrate specificities of matrix metalloproteinases-9 and -2, Biochem, J., 2005, vol. 392, pp. 127-134.
Steffensen et al., Extracellular Matrix Binding Properties of Recombinant Fibronectin Type II-like Modules of Human 72-kDa Gelatinase/Type IV Collagenase, 1995, vol. 270(19), pp. 11555-11566.
International Search Report and Written Opinion for PCT/GB2019/050917 dated Jul. 23, 2019, 17 pages.
Mikhailova et al., Identification of collagen binding domain residues that govern catalytic activities of matrix metalloproteinase-2 (MMP-2), Matrix Biology, 2012, vol. 31(7-8), pp. 380-388.
Steffensen et al., Human fibronectin and MMP-2 collagen binding domains compete for collagen binding sites and modify cellular activation of MMP-2, Matrix Biology, 2002, vol. 21(5) pp. 399-414.
Hollander et al., Damage to type II collagen in aging and osteoarthritis starts at the articular surface, originates around chondrocytes, and extends into the cartilage with progressive degeneration, The Journal of Clinical Investigation, 1995, vol. 96(6), pp. 2858-2869.
Zwolanek et al., β1 Integrins Mediate Attachment of Mesenchymal Stem Cells to Cartilge Lesions, BioResearch Open Access, 2015, vol. 4(1), pp. 39-53.

* cited by examiner

*Primary Examiner* — Anand U Desai
(74) *Attorney, Agent, or Firm* — Linda B. Huber; Nixon Peabody LLP

(57) ABSTRACT

Provided are peptides, and conjugates comprising targeting peptides and payloads. The peptides comprise a plurality of modules corresponding to at least one of module 1, module 2, or module 3 of the collagen binding domain of a gelatinase, or a gelatin-binding fragment or variant thereof. The gelatinase may be MMP-2. The conjugates may be therapeutic or non-therapeutic. Medical uses of the peptides or therapeutic conjugates, and pharmaceutical compositions comprising these, are also provided, as are nucleic acids encoding the peptides.

20 Claims, 10 Drawing Sheets

Specification includes a Sequence Listing.

SUMO CBD

CBD

A

B

Kd: 20.6 ± 4.1 nM (n=3)

PEPTIDES AND CONJUGATES

CROSS-REFERENCE TO RELATED APPLICATIONS

This application is a National Phase of International Application No. PCT/GB2019/050917, filed Mar. 29, 2019, which designated the U.S. and that International Application was published under PCT Article 21 (2) in English. This application also includes a claim of priority under 35 U.S.C. § 119 (a) and § 365 (b) to British patent application No. GB 1805306.6, filed Mar. 29, 2018, and to British patent application No. GB 1817486.2, filed Oct. 26, 2018, the contents of which are herein incorporated by reference in their entirety.

FIELD OF THE INVENTION

The present invention relates to peptides, and to conjugates comprising targeting peptides and payloads. The conjugates may be therapeutic or non-therapeutic. The invention also relates to the medical uses of the peptides or therapeutic conjugates, and to pharmaceutical compositions comprising these. Furthermore, the invention relates to nucleic acids encoding the peptides.

INTRODUCTION

Collagens are a large family of triple helical proteins that are widespread throughout the body and are important for a broad range of functions, including tissue scaffolding, cell adhesion, cell migration, cancer, angiogenesis, tissue morphogenesis and tissue repair. Collagen is the principal tensile element of vertebrate tissues such as tendon, cartilage, bone and skin.

Collagen may be classified with respect to its structure, whether it is fibrillar or non-fibrillar, or with respect to a number of different "types". The most abundant collagen in the human body is collagen type I, which is classified as a fibrillar collagen. Other types of fibrillar collagen are type II, III, V and XI. Of these type II collagen is the major collagenous component of cartilage.

Gelatin is formed on the breakdown of collagen by hydrolysis. This process is irreversible, but leaves degradation products that share sequence, and certain structural similarities, with the undigested collagen. Degradation of collagen, and corresponding accumulation of gelatin, may be associated with certain diseases.

In view of the importance of type II collagen to the structure of cartilage it will be appreciated that disorders associated with the breakdown of cartilage may be particularly associated with generation or accumulation of type II collagen gelatin. The generation or accumulation of type I collagen gelatin may be associated with disorders of a number of connective tissues, including the skin.

Matrix metalloproteinase 2 (MMP-2), also known as gelatinase A, binds to and cleaves gelatin, fragmenting it and clearing it from a degrading tissue. MMP-2 binds to gelatin through its Collagen Binding Domain (CBD).

Matrix metalloproteinase 9 (MMP-9), also known as gelatinase B, also binds to and cleaves gelatin. Again, MMP-9 binds to gelatin through its CBD.

It is known that the injection of mesenchymal stem cells (MSCs) into the joints of ageing osteoarthritis patients, can lead to a reduction in pain, however there is no evidence of MSC engraftment into cartilage. There is a therapeutic need for the clinical efficacy of MSC therapy to be enhanced in patients with osteoarthritis.

SUMMARY OF THE INVENTION

According to a first aspect of the invention, there is provided a peptide comprising a plurality of modules corresponding to at least one of module 1, module 2, or module 3 of the collagen binding domain of a gelatinase, or a gelatin-binding fragment or variant thereof.

According to a second aspect of the invention, there is provided a conjugate comprising a targeting peptide and a payload, wherein the targeting peptide comprises one or more modules of the collagen binding domain of a gelatinase, or gelatin-binding fragments or variants thereof. The gelatinase may be MMP-2.

In a third aspect the invention provides a pharmaceutical composition comprising a peptide of the invention or a therapeutic conjugate of the invention, and a pharmaceutically acceptable carrier. Suitably, a pharmaceutical composition comprising a peptide of the first aspect of the invention or a therapeutic conjugate of the second aspect of the invention and a pharmaceutically acceptable carrier.

In a fourth aspect the invention provides a nucleic acid encoding a peptide of the invention. Suitably, a nucleic acid according to the fourth aspect of the invention encodes a peptide of the first aspect of the invention.

According to a fifth aspect of the invention, there is provided a peptide comprising a plurality of modules corresponding to at least one of module 1 or module 2 of the collagen binding domain (CBD) of matrix metalloproteinase-9 (MMP-9), or a gelatin-binding fragment or variant thereof.

According to a sixth aspect of the invention, there is provided a conjugate comprising a targeting peptide and a payload, wherein the targeting peptide comprises one or more modules of the collagen binding domain of MMP-9, or gelatin-binding fragments or variants thereof.

Peptides in accordance with the first aspect of the invention are suitable for use as targeting peptides in the conjugates of the second aspect of the invention. All of the considerations set out in respect of the peptides of the first aspect of the invention are also applicable to the targeting peptides to be used in conjugates of the second aspect of the invention.

Peptides in accordance with the fifth aspect of the invention are suitable for use as targeting peptides in the conjugates of the sixth aspect of the invention. All of the considerations set out in respect of the peptides of the fifth aspect of the invention are also applicable to the targeting peptides to be used in conjugates of the sixth aspect of the invention.

A peptide in accordance with the first aspect of the invention may comprise only modules corresponding to module 1 of the CBD of a gelatinase (or gelatin binding fragments or derivatives thereof). Suitably the gelatinase is MMP-2.

Alternatively, a peptide in accordance with the first aspect of the invention may comprise only modules corresponding to module 2 of the CBD of a gelatinase (or gelatin binding fragments or derivatives thereof). Suitably, the gelatinase is MMP-2.

In another suitable embodiment, a peptide in accordance with the first aspect of the invention may comprise only modules corresponding to module 3 of the CBD of a gelatinase (or gelatin binding fragments or derivatives thereof). Suitably the gelatinase is MMP-2.

A peptide in accordance with the fifth aspect of the invention may comprise only modules corresponding to module 1 of the CBD of MMP-9 (or gelatin binding fragments or derivatives thereof).

A peptide in accordance with the fifth aspect of the invention may comprise only modules corresponding to module 2 of the CBD of MMP-9 (or gelatin binding fragments or derivatives thereof).

Peptides and conjugates of the invention are suitable for medical use, and particular medical uses of the peptides and conjugates of the invention are described further below.

As discussed further below, any reference to "peptides of the invention" throughout the specification may, except for where the context requires otherwise, be taken as referring to peptides in accordance with the first aspect of the invention, or peptides in accordance with fifth aspect of the invention.

Similarly, any reference to "conjugates of the invention" throughout the specification may except for where the context requires otherwise, be taken as referring to conjugates in accordance with the second aspect of the invention, or conjugates in accordance with the sixth aspect of the invention.

Figure 1:
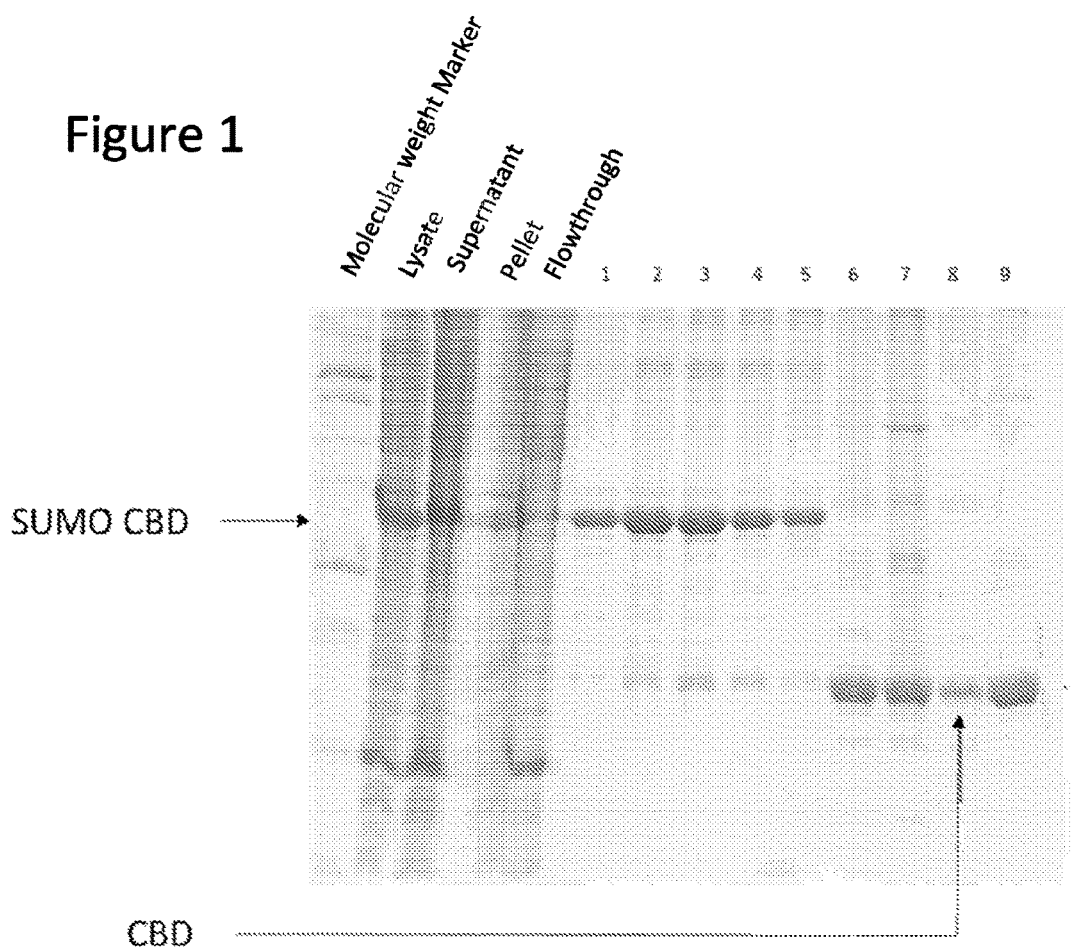
FIG. 1 shows SDS-PAGE gels of the expression and purification of the CBD of MMP-2 in Shuffle cells.
Figure 1:
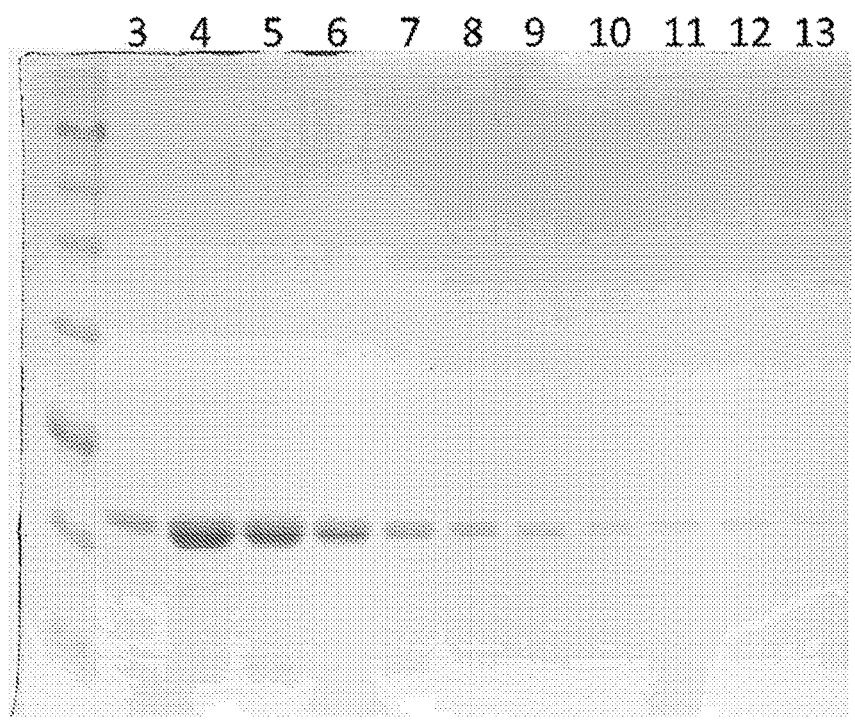

Table 1 shows the binding affinities for collagen type II and type I gelatin of the full length CBD of MMP-2, of individual modules of the CBD of MMP-2, of a peptide comprising three modules corresponding to module 2 (222), and of a peptide comprising three modules corresponding to module 3 (333). Binding affinity was measured by ELISA binding assay (Kd (nM)).

Table 2 shows a summary of all binding data, all ratios are protein:ligand.

Table 3 shows which residues of modules 1 and 2 of the CBD of MMP-2 were most important for binding to collagen type II gelatin following NMR analysis.

Table 4 shows the hydrodynamic radius and the zeta potential of a peptide, confirming that the two-step conjugation process was successful.

Table 5 shows predictions of the CBD residues involved in binding to Type II collagen based on published Type I collagen peptide data.

DETAILED DESCRIPTION OF THE INVENTION

The invention is based on the inventors' surprising findings regarding the relative importance for gelatin binding of different modules of the CBD of gelatinases. It is also based upon the highly surprising finding that it is possible to produce artificial peptides, based upon modules of the CBD of gelatinases, that have much higher binding affinity for particular forms of gelatin than do the native gelatinase CBDs themselves. In particular, the inventors have produced peptides of the invention that bind to type I or type II collagen gelatin with much higher affinity than either the native CBD from which they are derived (or individual modules making up the native CBD).

Previously published data on the CBDs of gelatinases, such as MMP-2, suggests that these bind to gelatin primarily through modules 2 and 3 with no substantial contribution from module 1. The prior art is also silent regarding the binding of the individual modules (modules 1, 2 or 3) of the CBD of gelatinases, such as MMP-2, to type II collagen gelatin.

The inventors have found that not only does the CBD of the gelatinase MMP-2 bind to type II collagen gelatin, but that this binding occurs primarily through modules 1 and 2, with no major contribution from module 3. As described further in the Examples, this surprising finding has been confirmed using two independent experimental methods (gelatin column binding and NMR analysis).

The identification of the importance of modules 1 and 2 in binding to type II collagen, and type II collagen gelatin, enables the use of peptides comprising these modules (or related fragment or variant sequences) for targeting of therapeutic or non-therapeutic payload bound to the peptides. This finding provides the basis for the conjugates disclosed in the second aspect of the invention.

Surprisingly, when the inventors investigated the properties of modules 1 and 2 further, they found that isolated forms of these modules demonstrated a reduction in binding affinity to gelatin, as compared to the wild type collagen binding domain of MMP-2.

Even more surprisingly, the inventors have found that a peptide comprising a plurality of modules corresponding to at least one of module 1, 2, or 3 of the collagen binding domain of a gelatinase, or a gelatin-binding fragment or variant thereof is able to demonstrate an increase in binding affinity when compared to the wild type collagen binding domain of the gelatinase from which the peptide is derived.

Of particular interest are peptides of the invention that comprise a total of three modules corresponding to module 1, module 2, or module 3 of the CBD of MMP-2 (or gelatin-binding fragments or derivatives of the native module).

Peptides of the invention comprising a total of three modules corresponding to module 2 of the CBD of MMP-2 have demonstrated particularly beneficial binding properties. The inventors have found that such peptides, as exemplified by the peptide of SEQ ID NO: 25, have a surprisingly high affinity for gelatin, in particular for type II collagen gelatin. As demonstrated in the Examples, peptides of the invention exemplified by SEQ ID NO: 25 have binding affinity for type II collagen gelatin that is approximately 14-fold higher than the binding of the naturally occurring CBD of MMP-2. Such peptides thus represent highly suitable targeting peptides to be employed in the conjugates of the invention.

The results that the inventors have produced also indicate that peptides of the invention comprising a total of three modules corresponding to module 3 of the CBD of MMP-2 will demonstrate advantageous gelatin binding activity. In this case, such peptides of the invention will provide agents that allow specific binding to type I collagen gelatin.

The ability of these peptides to bind with high affinity to gelatin, and particularly type II or type I collagen gelatin, enables them to target sites within the body where gelatin generation or accumulation is taking place. It will be appreciated that such generation or accumulation of gelatin is associated with locations at which damage to collagen is occurring.

In the case of gelatin derived from type II collagen, such sites are primarily associated with damage to cartilage, for example as a result of trauma, or degenerative disorders such as osteoarthritis. In the case of gelatin derived from type I collagen, such sites are typically associated with damage to the skin or connective tissue.

Accordingly, it will be appreciated that the production of novel peptides with high affinity for gelatin enables the targeting of these peptides, and also payloads associated with the peptides (such as in conjugates of the invention), to such sites of collagen damage. Thus, the peptides can be used to enable delivery of desired agents, such as therapeutic or imaging agents, to injured sites.

The use of therapeutic cells, such as mesenchymal stem cells, as therapeutic payloads to be delivered via conjugates of the invention is of particular interest. Mesenchymal stem cells are able to stimulate cartilage repair, but it has previously been difficult to ensure their accurate delivery to, and continued residency at, desired sites of damage.

As demonstrated in the Examples, conjugates of the invention comprising a peptide of the invention exemplified by SEQ ID NO: 25 also have a high binding affinity for type I collagen gelatin and type II collagen gelatin. Also demonstrated in the Examples, an exemplary conjugate of the invention comprising MSCs and a peptide exemplified by SEQ ID NO: 25 have a binding affinity for collagen type II gelatin that is approximately 10-fold higher than the binding of unconjugated MSCs. Thus, conjugates of the invention, such as those employing the peptides of the invention, provide valuable tools able to address this failing of the prior art.

The invention will now be further described, with reference to the following text, in which various terms used in the disclosure of the present invention are defined, Examples, and figures.

Except for where the context requires otherwise, definitions provided in respect of the peptides of the invention should also be considered to be applicable to the conjugates of the invention, and definitions provided in respect of the conjugates of the invention should also be considered to be applicable to the peptides of the invention. Medical uses and methods of treatment described herein may be relevant to both the peptides and conjugates.

The Collagen Binding Domain (CBD) of Gelatinases, and their Modules

The gelatinases (MMP-2, also known as gelatinase A, and MMP-9, also known as gelatinase B) are members of the matrix metalloproteinase family. The amino acid sequences of human MMP-2 and MMP-9 are set out in SEQ ID NO: 1 and 33 respectively.

The CBD of gelatinases confer the enzymes' ability to bind collagen, and products of collagen degradation such as gelatin. The residues of MMP-2 or MMP-9 making up the CBDs of these molecules are well known to those skilled in the art. For the avoidance of doubt, the amino acid sequence of the CBD of MMP-2 (gelatinase A) is set out in SEQ ID NO: 2, while the amino acid sequence of the CBD of MMP-9 (gelatinase B) is set out in SEQ ID NO: 31.

The CBDs of the gelatinases are made up of three modules: module 1, module 2, and module 3. With regard to the CBD of MMP-2, the amino acid sequence of module 1 is set out in SEQ ID NO: 6, the amino acid sequence of module 2 is set out in SEQ ID NO: 11 and the amino acid sequence of module 3 is set out in SEQ ID NO: 17. The amino acid sequences of modules 1, 2, and 3 of MMP-9 are set out in SEQ ID NOs: 34, 36, and 38.

As described in more detail elsewhere in the specification, the inventors have found that peptides of the invention can be manufactured that demonstrate high affinity binding for specific forms of gelatin. Surprisingly, the affinity demonstrated by these artificial peptides of the invention may be higher than the native CBDs from which they are derived, and also higher than the affinity shown by individual modules of the CBDs.

Except for where the context requires otherwise, peptides in accordance with the first aspect of the invention may comprise modules corresponding to modules of the CBD of MMP-2 or MMP-9. Suitably such peptides of the first aspect of the invention comprise modules corresponding to modules of the CBD of MMP-2.

In contrast, peptides in accordance with the fifth aspect of the invention comprise modules corresponding to modules of the CBD of MMP-9.

Modules "Corresponding" to a Module of the CBD of a Gelatinase

The three modules (1, 2, and 3) of the CBDs of the gelatinases MMP-2 or MMP-9 each have a distinctive characteristic sequence. Thus, these modules can each be distinguished from one another.

The amino acid sequences of modules 1, 2, and 3 of the CBD of MMP-2 are set out in SEQ ID NOs: 6, 11, and 17 respectively.

The amino acid sequences of modules 1, 2, and 3 of the CBD of MMP-9 are set out in SEQ ID NOs: 34, 36, and 38 respectively.

For the purposes of the present disclosure, a module may be said to correspond to one of modules 1, 2, or 3 of MMP-2 or MMP-9 if the module shares the same distinctive sequence as the native module. Furthermore, a sequence that is a variant of a particular module (1, 2, or 3) of MMP-2 or MMP-9 may also be said to correspond to that module if the variant module shares a higher percentage of sequence identity with the module in question than with the other modules. Thus, a module (such as a variant module) corresponds to module 1 of MMP-2 or MMP-9 if it shares a higher percentage sequence identity with module 1 than it does with either module 2 or module 3. In contrast a module corresponds to module 2 of MMP-2 or MMP-9 if it shares a higher percentage sequence identity with module 2 than it does with either module 1 or module 3. Finally, a module corresponds to module 3 of MMP-2 or MMP-9 if it shares a higher percentage sequence identity with module 3 than it does with either module 1 or module 2.

Suitably, exemplary amino acid sequences comprising modules that correspond to modules 1, 2 and 3 of the CBD of MMP-2 are set out in SEQ ID NOs: 7, 8, 12, 13, 14, 18, and 19.

Suitably, exemplary amino acid sequences comprising modules that correspond to modules 1, 2 and 3 of the CBD of MMP-9 are set out in SEQ ID NOs: 35, 37 and 30 respectively.

More details and characterisation of variants of modules of gelatinase CBDs are set out below.

Fragments of Modules

A fragment of a module is a sequence that shares 100% identity with a module of the CBD of a gelatinase, but is truncated in comparison to the native module. A fragment may comprise at least 10%, at least 25%, at least 50%, at least 60%, at least 70%, at least 75%, at least 80%, at least 85%, at least 90%, at least 95%, or more, of the full length of the corresponding native module. Suitably, a fragment may comprise at least 96%, at least 97%, at least 98%, at least 99% or more, of the full length of the corresponding native module.

Suitably, a fragment of a module may lack no more than 1 residue of a module of the CBD of a gelatinase. Alternatively, a fragment may lack no more than 2 residues, 3 residues, 4 residues, 5 residues, 6 residues, 7 residues, 8 residues, 9 residues or 10 residues of the full length module of the CBD of a gelatinase. Indeed, a suitable fragment may lack no more than 12 residues, 14 residues, 16 residues, 18 residues or no more than 20 residues of the full length module of the CBD of a gelatinase.

Variants of Modules or of Exemplary Sequences

Variants in the present context comprise at least one modification as compared to the amino acid sequence of a reference sequence. "Modification" as used herein refers to any change made to an amino acid sequence such that its sequence is not the same as that of the corresponding reference sequence. The reference sequence may, for example, be a native module or an exemplary sequence (such as an exemplary peptide of the invention).

Thus, a variant of a module is an amino acid sequence that share less than 100% homology with the sequence of a module of the CBD of a gelatinase, such as MMP-2 or MMP-9. For example, a suitable variant may share at least 70%, at least 75%, at least 80%, at least 85%, at least 90%, at least 95%, at least 96%, at least 97%, at least 98%, at least 99%, or more, identity with the sequence of the corresponding native module.

By the same token, a variant of an exemplary sequence is an amino acid sequence that shares less than 100% homology with an exemplary amino acid sequence, such as that of a particular peptide. For example, a suitable variant may share at least 70%, at least 75%, at least 80%, at least 85%, at least 90%, at least 95%, at least 96%, at least 97%, at least 98%, at least 99%, or more, identity with the sequence of the corresponding exemplary sequence.

It will be appreciated that a variant of a native module comprising such a modification is, by definition, not a native module. It will also be appreciated that a variant of an exemplary sequence will not share 100% identity with the exemplary sequence One or more modifications may be present in an amino acid sequence of a variant of a native module or exemplary sequence.

One or more different types of modification may be present in an amino acid sequence of a variant of a native module or exemplary sequence.

Modifications may, for example, comprise deletion of one or more amino acid residues found in the reference sequence, or addition of one or more amino acid resides not found in the reference sequence. Modifications may comprise substitutions of one or more amino acid residues with residues that do not correspond to those present in the reference sequence.

In a suitable embodiment, a variant, in the context of the present invention, may comprise a single modification as compared to the reference sequence. Alternatively, a variant may comprise at least 1 modification as compared to the reference sequence. Indeed, a variant for the purposes of the present disclosure may comprise at least 2 modifications, at least 3 modifications, at least 4 modifications, at least 5 modifications, at least 6 modifications, at least 7 modifications, at least 8 modifications, at least 9 modifications, at least 10 modifications, at least 15 modifications, or at least 20 modifications as compared to the reference sequence. A variant for the purposes of the present disclosure may even comprise at least 25 modifications, at least 30 modifications, at least 35 modifications, at least 40 modifications, at least 45 modifications, at least 50 modifications, as compared to the reference sequence.

Suitably, a variant for the purposes of the present disclosure may comprise up 2 modifications, up to 3 modifications, up to 4 modifications, up to 5 modifications, up to 6 modifications, up to 7 modifications, up to 8 modifications, up to 9 modifications, up to 10 modifications, up to 15 modifications, or up to 20 modifications as compared to the native amino acid sequence of the corresponding module. A variant for the purposes of the present disclosure may even comprise up to 25 modifications, up to 30 modifications, up to 35 modifications, up to 40 modifications, up to 45 modifications, or up to 50 modifications as compared to the native amino acid sequence of the corresponding module.

In a suitable embodiment, a peptide according to the first aspect of the invention may, comprise a variant of module 1, and/or a variant of module 2, and/or a variant of module 3 of the CBD of MMP-2.

Suitably, a peptide according to the first aspect of the invention may, comprise a variant of module 1, and/or a variant of module 2, and/or a variant of module 3 of the CBD of a gelatinase, such as MMP-2 or MMP-9.

In a suitable embodiment, a peptide according to the present invention may comprise a variant of module 1 of the CBD of a gelatinase, such as MMP-2 or MMP-9. For example, a variant of module 1 of the CBD of MMP-2 suitable for inclusion in a peptide of the invention may share at least 60%, at least 65%, at least 70%, at least 75%, at least 80%, at least 85%, at least 90%, or at least 95% identity to the amino acid sequence of the native module 1 (as defined by SEQ ID NO: 6). By the same token, a variant of module 1 of the collagen binding domain of MMP-9 suitable for inclusion in a peptide of the invention may share at least 60%, at least 65%, at least 70%, at least 75%, at least 80%, at least 85%, at least 90%, or at least 95% identity to the amino acid sequence of the native module (as defined by either SEQ ID NO: 34).

A peptide according to the present invention may suitably comprise a variant of module 2 of the CBD of a gelatinase, such as MMP-2 or MMP-9. For example, a variant of module 2 of the CBD of MMP-2 suitable for inclusion in a peptide of the invention may share at least 60%, at least 65%, at least 70%, at least 75%, at least 80%, at least 85%, at least 90%, or at least 95% identity to the amino acid sequence of the native module 2 (as defined by SEQ ID NO: 11). Similarly, a variant of module 2 of the collagen binding domain of MMP-9 suitable for inclusion in a peptide of the invention may share at least 60%, at least 65%, at least 70%, at least 75%, at least 80%, at least 85%, at least 90%, or at least 95% identity to the amino acid sequence of the native module (as defined by SEQ ID NO: 36).

In a suitable embodiment, a peptide according to the present invention may comprise a variant of module 3 of the CBD of a gelatinase, such as MMP-2 or MMP-9. For example, a variant of module 3 of the CBD of MMP-2 suitable for inclusion in a peptide of the invention may share at least 60%, at least 65%, at least 70%, at least 75%, at least 80%, at least 85%, at least 90%, or at least 95% identity to the amino acid sequence of the native module 3 as defined by SEQ ID NO: 17). By the same token, a variant of module 3 of the collagen binding domain of MMP-9 suitable for inclusion in a peptide of the invention may share at least 60%, at least 65%, at least 70%, at least 75%, at least 80%, at least 85%, at least 90%, or at least 95% identity to the amino acid sequence of the native module (as defined by SEQ ID NO: 38).

Suitably, a peptide according to the first aspect of the invention may comprise a variant module corresponding to module 1, module 2, or module 3 of the collagen binding domain of MMP-2, wherein at least one amino acid corresponding to residues 1 or 5 of SEQ ID NO: 14 is modified as compared to the corresponding residue of SEQ ID NO: 13.

For example, a peptide according to such an embodiment may comprise a variant wherein one or both of the residues corresponding to residues 1 and 5 of SEQ ID NO: 14 are substituted with valine and tyrosine respectively. Such a peptide may comprise or consist of the sequence set out in SEQ ID NO: 13.

Such variant forms of module 2 comprising modifications at either or both of the residues corresponding to residues 1 and 5 of SEQ ID NO: 14 may be incorporated as the module closest to the N-terminal of a peptide of the invention.

Suitably, a peptide of the invention may comprise or consist of a variant of the exemplary peptide set out in SEQ ID NO: 25.

It will be appreciated that a modification to an amino acid sequence may change the biological function of a peptide. By way of example, a modification to an amino acid sequence may increase or decrease the binding affinity of the peptide to gelatin.

Merely by way of example, the peptide of the invention comprising at least one modification of an amino acid corresponding to residues 19, 21, 31, 35, 38, 41, 45, or 51 of SEQ ID NO: 14 may demonstrate an increase in binding affinity to gelatin.

Thus, in a suitable embodiment, a peptide according to the first aspect of the invention comprises at least one amino acid corresponding to residues 19, 21, 31, 35, 38, 41, 45, or 51 of SEQ ID NO: 14 that is modified as compared to the corresponding residue of SEQ ID NO: 14.

Merely by way of example, such a peptide according to the first aspect of the invention may comprise at least one amino acid corresponding to residues 19, 21, 31, 35, 38, 41, 45, or 51 of SEQ ID NO: 14 that is substituted for an alternative amino acid as compared to the corresponding residue of SEQ ID NO: 14.

In a suitable embodiment, such a peptide according to the first aspect of the invention may comprise at least one amino acid corresponding to residues 21, 31, 35, 38, 41 or 45 of SEQ ID NO: 14 that is modified as compared to the corresponding residue of SEQ ID NO: 14.

Alternatively, the peptide according to the first aspect of the invention, may comprise at least one amino acid corresponding to residues 19 or 51 of SEQ ID NO: 3 that is modified as compared to the corresponding residue of SEQ ID NO: 14.

A peptide in accordance with the first aspect of the invention may comprise at least one modification of an amino acid residue corresponding to one or more of the residues identified in Tables 3 or 5.

Gelatin Binding Fragments and Gelatin Binding Variants of Modules

Gelatin binding fragments and gelatin binding variants of modules of the CBD of a gelatinase (such as MMP-2 or MMP-9) may be determined by their ability to bind to gelatin.

Methods for determining whether a fragment or variant of a module of the CBD of a gelatinase has the ability to bind to gelatin will be known by the skilled person.

Suitable examples of methods for determining whether a fragment or variant of a module of CBD of a gelatinase is able to bind to gelatin are set out in the Examples section. These include assays investigating the binding of fragments or variants to gelatin sepharose, and assays based on NMR analysis. The methods described in the Examples section also allow the skilled person to determine the binding constant of fragments or variants of modules of the CBD of a gelatinase.

Peptides

As referred to above, the first aspect of the invention relates to peptides. In particular, the first aspect of the invention relates to a peptide that comprises a plurality of modules corresponding to at least one of module 1, module 2, or module 3 of the collagen binding domain of MMP-2, or a gelatin-binding fragment or variant thereof.

In a suitable embodiment, a peptide according to the first aspect of the invention may comprise a plurality of modules corresponding to module 2 of the collagen binding domain of MMP-2, or gelatin-binding fragments or variant thereof. Suitably, the peptide may comprise a total of two, three, four, five, six, seven, eight, nine or ten modules corresponding to module 2 of the collagen binding domain of MMP-2, or gelatin-binding fragments or variant thereof. Such a peptide may comprise further modules that do not correspond to module 2 (such as modules corresponding to module 1 and/or module 3 of MMP-2, or modules corresponding to those of the CBD of another gelatinase). Alternatively, a peptide in accordance with such an embodiment may lack such further modules.

In a suitable embodiment, a peptide according to the first aspect of the invention may comprise a total of three modules corresponding to module 2 of the collagen binding domain of MMP-2, or gelatin-binding fragments or variant thereof. As referred to above, such peptides of the invention, as exemplified by the peptide of SEQ ID NO: 25, demonstrate an unexpectedly high binding affinity for gelatin. In particular peptides in accordance with this embodiment of the invention demonstrate an unexpectedly high binding affinity for type II collagen gelatin. Accordingly, peptides comprising or consisting of SEQ ID NO: 25, or fragments or variants thereof, are considered particularly useful embodiments of the peptides of the invention.

Peptides in accordance with this embodiment of the invention may lack further modules corresponding to either module 1 or 3 of the CBD of MMP-2. Accordingly, the only modules corresponding to modules of MMP-2's CBD may be the three modules corresponding to module 2. It will be appreciated that, in the case that such a peptide of the invention comprises a number of modules that are variants of module 2 of the CBD of MMP-2, these modules may be identical to one another, or may differ between one another. More details of exemplary peptides in accordance with this embodiment are set out below.

In a suitable embodiment, a peptide according to the first aspect of the invention may comprise a plurality of modules corresponding to module 1 of the collagen binding domain of MMP-2, or gelatin-binding fragments or variant thereof. Suitably, the peptide may comprise a total of two, three, four, five, six, seven, eight, nine or ten modules corresponding to module 1 of the collagen binding domain of MMP-2, or gelatin-binding fragments or variant thereof. Such a peptide may comprise further modules that do not correspond to module 1 (such as modules corresponding to module 2 and/or module 3 of the CBD of MMP-2, or to modules of the CBD of another gelatinase). Alternatively, a peptide in accordance with such an embodiment may lack such further modules.

In a suitable embodiment, a peptide according to the first aspect of the invention may comprise a total of three modules corresponding to module 1 of the collagen binding domain of MMP-2, or gelatin-binding fragments or variant thereof. An example of the amino acid sequence of such a peptide of the invention is set out in SEQ ID NO: 22. Peptides in accordance with this embodiment of the invention may demonstrate high affinity binding for type II collagen gelatin. Peptides comprising or consisting of SEQ ID NO: 22, or fragments or variants thereof, are also considered particularly useful embodiments of the peptides of the invention.

Peptides in accordance with this embodiment of the invention may lack further modules corresponding to either module 2 or 3 of the CBD of MMP-2. Accordingly, the only modules corresponding to modules of the MMP-2 CBD may be the three modules corresponding to module 1. Again, in the event that such a peptide comprises variant modules, each variant module may be identical to one another, or the variant modules may differ from one another. More details of peptides exemplifying this embodiment of the invention are set out below.

A peptide according to the first aspect of the invention may suitably comprise a plurality of modules corresponding to module 3 of the collagen binding domain of MMP-2, or gelatin-binding fragments or variant thereof. Suitably, the peptide may comprise a total of two, three, four, five, six, seven, eight, nine or ten modules corresponding to module 3 of the collagen binding domain of MMP-2, or gelatin-binding fragments or variant thereof. Such a peptide may comprise further modules that do not correspond to module 3 (such as modules corresponding to module 1 and/or module 2 of MMP-2, or modules corresponding to those of the CBD of another gelatinase). Alternatively, a peptide in accordance with such an embodiment may lack such further modules.

In a suitable embodiment, a peptide according to the first aspect of the invention may comprise a total of three modules corresponding to module 3 of the collagen binding domain of MMP-2, or gelatin-binding fragments or variant thereof. Peptides in accordance with this embodiment of the invention, as exemplified by the peptide of SEQ ID NO: 27, demonstrate an unexpectedly high binding affinity for gelatin, and in particular an unexpectedly high binding affinity for type I collagen gelatin. Suitably the invention provides a peptide comprising or consisting of SEQ ID NO: 27, or fragments or variants thereof.

Peptides in accordance with this embodiment of the invention may lack further modules corresponding to either module 1 or 2 of the CBD of MMP-2. Accordingly, the only modules corresponding to modules of MMP-2's CBD may be the three modules corresponding to module 3. It will be appreciated that, in the case that such a peptide of the invention comprises a number of modules that are variants of module 3 of the CBD of MMP-2, these modules may be identical to one another, or may differ between one another. More details of exemplary peptides in accordance with this embodiment are set out below.

Suitably, a peptide according to the first aspect of the invention may comprise a plurality of modules corresponding to both module 1 and module 2 of the collagen binding domain of MMP-2, or gelatin-binding fragments or variant thereof. Indeed, a peptide according to the first aspect of the invention may comprise a plurality of both module 1 and module 2 of the collagen binding domain of MMP-2, or gelatin-binding fragments or variant thereof.

Suitably, a peptide according to the first aspect of the invention may demonstrate an increase in binding affinity to gelatin when compared to the wild type collagen binding domain of MMP-2. In a suitable embodiment, a peptide according to the first aspect of the invention may demonstrate a binding affinity to gelatin that is increased in magnitude by between 2-fold and 100-fold when compared to binding by the wild type collagen binding domain of MMP-2. Merely by way of example, a suitable peptide in accordance with the invention may have a binding affinity that is increased by at least 2-fold, at least 3-fold, at least 4-fold, at least 5-fold, least 6-fold, at least 7-fold, at least 8-fold, at least 9-fold, least 10-fold, at least 11-fold, at least 12-fold, at least 13-fold, least 14-fold, or at least 15-fold increased as compared to the affinity of the CBD of native MPP-2. Indeed, a suitable peptide in accordance with the invention may have a binding affinity that is increased by at least 20-fold, at least 25-fold, at least 50-fold or at least 75-fold increased as compared to the affinity of the CBD of native MPP-2.

Such increases in binding affinity may be particularly noted with respect to the affinity of peptides for type II collagen gelatin (for example, in the case of peptides comprising repeated modules corresponding to module 1 or 2 of the CBD of MMP-2), or with respect to the affinity of the peptides for type I collagen gelatin (for example, in the case of peptides comprising repeated modules corresponding to module 2 or 3 of the CBD of MMP-2).

By way of specific example, the inventors have found that a peptide of the invention comprising a total of three modules corresponding to module 2 of the collagen binding domain of MMP-2, or gelatin-binding fragments or variant thereof (exemplified by the peptide of SEQ ID NO: 25) demonstrates a binding affinity for type II collagen gelatin that is 14-fold higher than that of the naturally occurring CBD of MMP-2.

A peptide of the invention may comprise or consist of the amino acid sequence set out in SEQ ID NO: 25.

A peptide of the invention may comprise or consist of the amino acid sequence set out in SEQ ID NO: 22.

A peptide of the invention may comprise or consist of the amino acid sequence set out in SEQ ID NO: 27.

Alternatively, a peptide of the invention may comprise a fragment of the amino acid sequence set out in SEQ ID NO: 25, SEQ ID NO: 22, or SEQ ID NO: 27. Further, a suitable peptide of the invention may comprise or consist of a variant of the peptide set out in SEQ ID NO: 25, the peptide set out in SEQ ID NO: 22, or the peptide set out in SEQ ID NO: 27.

Merely by way of example, a suitable variant may share at least 85%, at least 86%, at least 87%, at least 88%, at least 89%, at least 90%, at least 91%, at least 92%, at least 93%, at least 94%, at least 95%, at least 99%, or more, sequence identity with the amino acid sequence set out in SEQ ID NO: 25, SEQ ID NO: 22, or SEQ ID NO: 27.

A suitable peptide of the invention may comprise or consist of a variant of the peptide set out in SEQ ID NO: 25, SEQ ID NO: 22, or SEQ ID NO: 27 that varies from SEQ ID NO: 25, 22, or 27 by no more than 1 modification, or by no more than 2, 3, 4, 5, 6, 7, 8, 9, or 10 modifications.

Specific Variants of Modules Incorporated in the Exemplary Peptides of SEQ ID NO: 25 (222), SEQ ID NO: 22 (111), or SEQ ID NO: 27 (333)

The sequences of three peptides of the invention, herein referred to as 111, 222 and 333 are set out in SEQ ID NOs: 22, 25, and 27 respectively. Peptide 111 comprises a total of three modules corresponding to module 1 of the collagen binding domain of MMP-2. Peptide 222 comprises a total of three modules corresponding to module 2 of the collagen binding domain of MMP-2. Peptide 333 comprises a total of three modules corresponding to module 3 of the collagen binding domain of MMP-2.

In each case, the modules incorporated in the peptides (111, 222, or 333) of the invention comprise variants of the sequences of the naturally occurring modules. The variant modules employed in these exemplary peptides of the invention may be utilised in other peptides or conjugates in accordance with this disclosure. Variant modules employed in these exemplary peptides are set out in SEQ ID NO: 8 (variant of module 1 of CBD of MMP-2), SEQ ID NO: 14 (variant of module 2 of CBD of MMP-2), and SEQ ID NO: 19 (variant of module 3 of CBD of MMP-2).

In particular, the second of the three modules present in a peptide of the invention may be modified by substitution of naturally occurring amino acid residues with residues from the corresponding site in the naturally occurring sequence of module 2 of a gelatinase CBD. Merely by way of example, this is shown in the sequence of 111, where methionine and arginine residues have been introduced in the second module corresponding to module 1 (at residues 66 and 99 of SEQ ID NO: 22, respectively).

Without wishing to be bound by any hypothesis, the inventors believe that the inclusion of substitutions in this manner is able to improve activity of a peptide of the invention. In particular, the inventors believe that the incorporation of these substitutions, optionally in combination with the incorporation of linker sequences (as discussed further below) in peptides of the invention facilitates the formation of intramolecular interactions that stabilise the arrangement of modules 1 and 2 within the peptide. This increased stability may promote gelatin binding by the peptides.

In light of the above, it will be appreciated that corresponding modifications may be introduced into other modules constituting variants to be used in the peptides or conjugates of the invention.

Linker Sequences

In a suitable embodiment, a peptide according to the invention may comprise at least one linker sequence flanking at least one of the modules. Suitably, the peptide may comprise one, two, three, four or more linker sequences flanking modules of the CBD of a gelatinase, or gelatin-binding fragments or variants thereof.

In a suitable embodiment, a peptide according to the invention may comprise at least one linker sequence selected from the group consisting of: linker sequence 2 (amino acid residues HEA), linker sequence 3 (amino acid residues ETA), SEQ ID NO: 29 (linker sequence 1-amino acid residues EGQV), SEQ ID NO: 31, and SEQ ID NO: 32. By way of example, a peptide may comprise linker sequences comprising each of SEQ ID NOs: 29, 32, linker sequence 2 and linker sequence 3. Such a peptide may comprise single or multiple copies of one, more than one, or all of the linker sequences.

Conjugates

The second and sixth aspects of the invention relate to conjugates. These comprise a targeting peptide and a payload, both of which are defined in more detail below.

The targeting peptide and payload are joined, to produce a conjugate of the invention. This allows the targeting peptide to control the sites to which the conjugate, and thus the payload, bind.

The targeting peptide and payload may be conjugated by any suitable means known by those skilled in the art. Merely by way of illustration, the targeting peptide and payload may be conjugated to one another by means of a polymer-surfactant complex. An example of a suitable technique for such polymer-surfactant conjugation is disclosed in a publication by J. P. K. Armstrong et al., (Nature Communications 2015, 6:7405). In this technique, also described further in the Examples section of this specification, the membrane affinity of protein—surfactant complexes are designed to display an amphiphilic polymer-surfactant corona to facilitate delivery to the cytoplasmic membrane.

A conjugate in accordance with the second or sixth aspects of the invention may comprise a plurality of targeting peptides and/or a plurality of payloads. Thus, in a suitable embodiment a conjugate of the invention may comprise a single targeting peptide and a plurality of payloads. Alternatively, a suitable conjugate may comprise a plurality of targeting peptides and a single payload.

Targeting Peptides

Targeting peptides are peptides that serve to direct the binding of conjugates in accordance with the second or sixth aspects of the invention. In particular, targeting peptides may be capable of binding to collagen or to gelatin produced on the degradation of collagen.

Targeting peptides suitable for use in the conjugates of the second or sixth aspect of the invention may be capable of binding to collagen or gelatin, and in particular to type I or type II collagen gelatin. In particular, they may exhibit specific binding to a particular form of collagen or gelatin, such as type I or type II collagen gelatin.

Merely by way of example, targeting peptides comprising a plurality of modules corresponding to module 2 or module 1 of the CBD of a gelatinase may be useful in specifically binding to type II collagen gelatin. Targeting peptides comprising a plurality of modules corresponding to module 2 or module 3 of the CBD of a gelatinase may be useful in specifically binding to type I collagen gelatin. While peptides comprising a plurality of modules corresponding to module 2 have high affinity for both type I collagen gelatin and type II collage gelatin, it will be appreciated that there are many body sites where effective targeting can still be achieved due to the local prevalence of either type I or type II collagen.

Suitable examples of targeting peptides include, but are not limited to, peptides in accordance with the first or fifth aspects of the invention. The various considerations set out in this disclosure regarding embodiments of peptides in accordance with the first or fifth aspects of the invention should also be taken as applicable and disclosed in relation to targeting peptides for use in the conjugates of the second or sixth aspects of the invention.

As set out in the second and sixth aspects of the invention, targeting peptides suitable for use in conjugates disclosed herein comprise one or more modules of the CBD of a gelatinase, or gelatin-binding fragments or variants thereof. It will be appreciated that naturally occurring forms of the CBD of a gelatinase (such as MMP-2 or MMP-9), or fragments of such naturally occurring forms, will also constitute targeting peptides that may be incorporated in conjugates in accordance with the second or sixth aspects of the invention.

Examples of the peptides of the invention may be used as targeting peptides able to confer specificity of binding on a conjugate in accordance with the invention. For example, a peptide in accordance with the first aspect of the invention, comprising a plurality of modules corresponding to module 1 of the CBD of MMP-2 (as exemplified by the peptide of SEQ ID NO: 22) may be used as a targeting peptide to target conjugates of the invention to locations at which collage type II gelatin is being generated or accumulated. Similarly, a peptide in accordance with the first aspect of the invention, comprising a plurality of modules corresponding to module 2 of the CBD of MMP-2 (as exemplified by the peptide of SEQ ID NO: 25) may be used as a targeting peptide to target conjugates of the invention to locations at which collage type II gelatin is being generated or accumulated. Alternatively, a peptide in accordance with the first aspect of the invention, comprising a plurality of modules corresponding to module 3 of the CBD of MMP-2 (as exemplified by the peptide of SEQ ID NO: 27) may be used as a targeting peptide to target conjugates of the invention to locations at with collage type I gelatin is being generated or accumulated. Examples of conditions associated with the generation or accumulation of type I or type II collagen gelatin are discussed elsewhere in this specification.

Payloads

The payload referred to in connection with the conjugates of the invention comprises a cargo to be provided to a specific site. The targeting peptide confers specificity in respect of the site to which the cargo is provided.

In a suitable embodiment, the payload comprises a cargo to be targeted to gelatin. Suitably the gelatin may be type II collagen gelatin. Alternatively, the gelatin may be type I collagen gelatin. Targeting peptides that may be used in such embodiments are described in more detail above.

In a suitable embodiment, the payload may be therapeutic or non-therapeutic. These alternatives are discussed in more detail below.

The payload may be a naturally occurring payload or a synthetic payload.

A conjugate in accordance with the second or sixth aspects of the invention may comprise a single payload, or a plurality of payloads. In an embodiment where a conjugate of the invention comprises a plurality of payloads these may be a plurality of identical payloads or of different payloads.

Merely by way of example, a plurality of payloads may provide synergistic benefits.

A Therapeutic Payload

A therapeutic payload may provide treatment of a condition in a subject. Suitably, a therapeutic payload may reduce symptoms of a condition in a subject. Alternatively, or additionally, a therapeutic payload may delay the onset of a given condition in a given subject.

The therapeutic capacity of a payload may be assessed in relation to the symptoms of a subject in need of treatment. Thus, a therapeutic payload is one capable of treatment of a given condition of a given subject.

As discussed further below, a suitable therapeutic payload may be selected from the list consisting of: a therapeutic cell; a therapeutic drug molecule; a therapeutic growth factor.

A Therapeutic Cell

In a suitable embodiment, a therapeutic payload may comprise a therapeutic cell.

A therapeutic cell may provide treatment of a condition in a subject. A therapeutic cell may provide treatment directly (through the action of the therapeutic cell itself, such as by integration and replication at a site of damage associated with the condition), and/or indirectly (through the influence of the therapeutic cell on other cells, where these influenced cells then serve to resolve the condition).

An example of direct treatment of a given condition may be by cellular differentiation of the therapeutic cell at the site to which the payload is provided.

In contrast, indirect treatment may be provided by the production of trophic factors by the therapeutic cell. Examples of such trophic factors include VEGF; CNTF; GDNF; TGF-β; interleukins (such as, IL-1β, IL-6, and IL-8); and C-C ligands (such as, CCL-2, CCL-5, and CCL-23).

Suitably, a therapeutic cell may be an autologous cell. Alternatively, or additionally, a therapeutic cell may be an allogeneic cell.

Suitably, a therapeutic cell may be selected from the group consisting of; a stem cell; and a chondrocyte.

In a suitable embodiment, a therapeutic payload comprises a stem cell. A suitable stem cell may be selected from the group consisting of; a mesenchymal stem cell (MSC); an induced pluripotent stem cell (iPSC); an umbilical cord stem cell; and an embryonic stem cell.

Suitably, a mesenchymal stem cell may be an autologous MSC or an allogeneic MSC.

An MSC represents a particularly suitable payload for incorporation in a conjugate for medical use in the prevention and/or treatment of osteoarthritis. In a suitable embodiment, a conjugate according to the second aspect of the invention may comprise a targeting peptide and a therapeutic payload, wherein the therapeutic payload is an allogeneic mesenchymal stem cell. Suitably, such a conjugate may comprise a plurality of targeting peptides. Suitably the targeting peptides may comprise or consist of the amino acid sequence set out in SEQ ID NO: 25. Alternatively, the targeting peptides may comprise or consist of the amino acid sequence set out in SEQ ID NO: 22.

Suitably, an example of a therapeutic cell may be a chondrocyte. A chondrocyte may provide treatment of a condition in a subject directly, for example by integration into the targeted tissue.

It will be appreciated that an exemplary conjugate of the invention comprising an MSC payload and a targeting peptide (such as SEQ ID NO:25) may have particular utility in the prevention or treatment of osteoarthritis. An in vitro model demonstrating the binding of such conjugates to type II collagen gelatin, which is known to be present at the articular surface of osteoarthritic joints, is set out in Example 8, below.

A Therapeutic Drug Molecule

In a suitable embodiment, the therapeutic payload may comprise a therapeutic drug molecule. Such a therapeutic drug molecule may be selected on the basis of its ability to provide treatment of a condition in a subject.

A therapeutic drug molecule may act to inhibit a metabolic pathway associated with a given condition. Additionally, or alternatively, a therapeutic drug molecule may act to enhance a metabolic pathway associated with a given condition.

A therapeutic drug may stimulate cellular differentiation, cellular proliferation or apoptosis in a tissue associated with a given condition.

Suitably, a therapeutic drug molecule may be selected from the group consisting of: an anti-inflammatory agent; a proteinase inhibitor; and an anti-proliferative agent.

Suitably, a therapeutic drug molecule may comprise an anti-inflammatory agent.

In a suitable embodiment, the therapeutic payload may comprise a corticosteroid.

Suitably a therapeutic drug molecule may comprise a proteinase inhibitor. In a suitable embodiment such a proteinase inhibitor may be selected from the group consisting of: a metalloproteinase inhibitor; a serine proteinase inhibitor; and a cysteine proteinase inhibitor.

Hydroxamate-type metalloproteinase inhibitors constitute examples of therapeutic drug molecules that may be used as payloads in the conjugates of the invention. Hydroxamate-type MMP inhibitors may be used in the prevention and/or treatment of degenerative conditions such as arthritis. Previous attempts to employ hydroxamate-type MMP inhibitors therapeutically have been limited due to side effects of the compounds. The inventors believe that the improved targeting that can be achieved in respect of conjugates of the invention will enable side effects of these compounds to be reduced, thus making their therapeutic use more practical.

A Therapeutic Growth Factor

In a suitable embodiment, the therapeutic payload may comprise a therapeutic growth factor. A suitable therapeutic growth factor may be selected on the basis of its ability to provide treatment of a given condition of a given subject.

By way of example, a growth factor may provide treatment of a given condition of a given subject by influencing cells associated with the condition.

By way of example, a growth factor may influence a cell associated with a given condition by means of influencing on or more of: cellular growth; and/or cellular proliferation; and/or cellular differentiation; and/or cellular maturation.

Suitably, a growth factor to be used as a payload in a conjugate of the invention may be a protein or a hormone.

A suitable example of a therapeutic growth factor may be selected from the group consisting of: transforming growth factor beta (TGF-β); and fibroblast growth factor (FGF2)

A Non-Therapeutic Payload

In a suitable embodiment, the payload may be a non-therapeutic payload.

Suitably, a non-therapeutic payload may be selected from the group consisting of: a contrast agent; a dye agent; and a radio-labelled agent.

Suitably, a contrast agent may have particular utility in imaging.

Conjugate Binding

Conjugates according to the second or sixth aspects of the invention comprising a payload and target peptide may demonstrate an increase binding affinity for gelatin. A conjugate comprising a therapeutic cell payload (such as an MSC) and a targeting peptide of the invention may demonstrate a higher affinity for gelatin than an unconjugated MSC. By way of example, a conjugate of the invention comprising an MSC payload and a targeting peptide comprising three modules of module 2 of the CBD of MMP-2 (222) may demonstrate a higher binding affinity for gelatin (in particular collagen type II gelatin) than an unconjugated control MSC.

The inventors have demonstrated that exemplary conjugates of the invention comprising an MSC payload and a 222 targeting peptide have higher binding affinity for collagen type II gelatin than they do for tissue culture plastic. As shown in Example 8, exemplary conjugates of the invention comprising an MSC payload and a 222 targeting peptide demonstrate a 224% higher binding in the number of conjugates that bind to collagen type II gelatin compared to those bound to plastic.

It will be appreciated that a conjugate of the invention comprising an MSC payload and a 222 targeting peptide (of SEQ ID NO:25) may have particular utility in prevention and/or treatment of a disorder associated with generation or accumulation of gelatin, and particularly type II collagen gelatin. It was previously shown that type II collagen gelatin is found at the articular surface in osteoarthritic joints (Hollander et. al, "Damage to type II collagen in aging and osteoarthritis starts at the articular surface, originates around chondrocytes, and extends into the cartilage with progressive degeneration" J Clin Invest. 1995 December; 96(6): 2859-69). It will be appreciated that MSCs may provide useful therapeutic agents for use in the treatment of osteoarthritis.

Disorders and Medical Uses

The peptides of the first or fifth aspects of the invention, or therapeutic conjugates of the second or sixth aspects of the invention are suitable for use as medicaments.

Suitably the peptides or conjugates may be used in the prevention and/or treatment of a disorder associated with generation or accumulation of gelatin.

By way of example, the disorder may be a disease or injury. In a suitable embodiment, the disorder is a disease or injury of a soft tissue. Suitably the soft tissue may be selected from the group consisting of: cartilage; myocardium; the cornea; and an intervertebral disc.

A peptide or conjugate of the invention may be used in the prevention and/or treatment of osteoarthritis. This is somewhat counterintuitive, since it is known that gelatinases contribute to the development of osteoarthritis. MSCs, as considered above, represent particularly suitable therapeutic payloads for use in such embodiments.

A peptide or conjugate of the invention may also be used in the prevention and/or treatment of spinal intervertebral disc degeneration.

In an embodiment, a peptide of the first aspect of the invention set out in SEQ ID NO: 25 may be used in the prevention and/or treatment of osteoarthritis, or in the prevention and/or treatment of spinal intervertebral disc degeneration.

Suitably a peptide or conjugate of the invention may be used in the prevention and/or treatment of myocardial infarction. In particular, a peptide or conjugate of the invention may be used in the prevention and/or treatment of myocardial damage after myocardial infarction.

In a suitable embodiment a peptide or conjugate of the invention may be used in the prevention and/or treatment of corneal ulcer. Corneal ulcer has been reported to be associated with collagen degradation, and hence with generation or accumulation of gelatin.

The skilled reader will appreciate that appropriate peptides or conjugates of the invention for medical uses may be selected with reference to the form of gelatin generated or accumulated.

For example, in the case of a disorder associated with the generation or accumulation of type II collagen gelatin, an appropriate peptide or conjugate for medical use may comprise a plurality of modules corresponding to module 1 or module 2 of a gelatinase CBD. It will be appreciated that the generation or accumulation of type II collagen gelatin is associated with osteoarthritis and spinal intravertebral disc degeneration, and with disorders in which cartilage is broken down. Suitable peptides for use in such applications may include those of SEQ ID NO: 25 or SEQ ID NO: 22, or gelatin-binding fragments or variants of such peptides.

On the other hand, in the case of a disorder associated with the generation or accumulation of type I collagen gelatin, an appropriate peptide or conjugate for medical use may comprise a plurality of modules corresponding to module 3 of a gelatinase CBD. It will be appreciated that myocardial damage after myocardial infarction and corneal ulcers both represent examples of disorders associated with the generation or accumulation of type I collagen gelatin. Suitable peptides for use in such applications may include those of SEQ ID NO: 27, or gelatin-binding fragments or variants of this exemplary peptide.

It will be appreciated that a peptide or conjugate of the invention may be used to promote repair or regeneration of a soft tissue. Stem cells, such as MSCs, represent suitable therapeutic payloads to be used in conjugates intended for such uses.

The methods of treatment or medical uses of the invention may be utilised in connection with known therapeutic regimes, such as surgery. They may be employed in respect of human or non-human animals. The methods of treatment or medical uses may be utilised in respect of adults, children or foetuses (for example, in the context of intra-uterine surgery).

Selection of Conjugates

Certain payloads that may be employed in conjugates of the invention, such as MSCs, are prone to non-specific binding to various materials. As shown in Example 8, unconjugated control MSCs demonstrate non-specific binding to plastic, such as tissue culture plastics.

The inventors have found that when such payloads are incorporated in conjugates of the invention, and particularly in such conjugates where the payload is coated with a peptide of the invention, the non-specific binding of the payload is reduced. For example, non-specific binding of MSCs to plastic was significantly reduced in conjugates of the invention comprising MSCs and targeting peptide, 222, where the cells are "coated" in the targeting peptide.

The ability of peptides of the invention to reduce non-specific binding of unconjugated payloads (such as MSCs) to materials such as plastic may be utilised in a method of selecting successfully formed conjugates of the invention. For example, such successfully formed conjugates may be selected from a population containing payloads that have not successfully formed conjugates. In the case of MSC payloads, such a population may include both conjugates comprising MSCs and unconjugated MSCs.

By way of example, a method of selecting a conjugate of the invention from a population of conjugated and unconjugated payloads may comprise;
 i) contacting the population of conjugated and unconjugated payloads with a surface capable of binding non-specifically to unconjugated payloads for a time sufficient for the unconjugated payloads to bind non-specifically to the surface,
 ii) separating the bound and unbound populations of payloads, to provide an enriched population of conjugated payloads.

The payloads may be therapeutic cells, such as MSCs. The surface capable of binding non-specifically to unconjugated payloads may be a tissue culture plastic. The time sufficient for binding may be between 1 and 48 hours.

In a more specific example, a method of selecting a conjugate of the invention from a population of conjugated and unconjugated MSC payloads may comprise;
 i) contacting the population of conjugated and unconjugated MSC payloads with a tissue culture plastic for a time sufficient for the unconjugated payloads to bind non-specifically to the tissue culture plastic,
 ii) separating the bound and unbound populations of payloads, to provide an enriched population of conjugated MSCs.

Pharmaceutical Compositions

In a third aspect the invention provides a pharmaceutical composition comprising a peptide of the first or fifth aspect of the invention or a therapeutic conjugate of the second or sixth aspect of the invention, and a pharmaceutically acceptable carrier.

A "pharmaceutically acceptable carrier", in the context of the present disclosure, refers to an ingredient, other than an active ingredient, in a pharmaceutical formulation in which the peptide or conjugate of the invention is dispersed. Such a carrier is suitably nontoxic to a subject receiving the composition. A suitable pharmaceutically acceptable carrier includes, but is not limited to, examples selected from the group consisting of: a buffer, an excipient, a stabilizer, or a preservative.

It will be appreciated that an appropriate carrier, and hence an appropriate pharmaceutical composition, may be selected on the basis of its ability to maintain, or promote, the activity of the therapeutic agent. Thus, an appropriate carrier may be selected with reference to the selected therapeutic payload. The skilled person will be aware of suitable carriers that may be used for the formulation of compositions comprising therapeutic cells, as well as suitable carriers that may be used for the formulation of compositions comprising therapeutic drug molecules or growth factors.

Nucleic Acids

In a fourth aspect the invention provides a nucleic acid encoding a peptide according the first or fifth aspect of the invention. Exemplary nucleic acids in accordance with this embodiment include those set out in the Sequence Information section below.

Merely by way of example, a nucleic acid in accordance with the invention may comprise one or more of the nucleic acid sequences set out in the sequence information section below. For example, a DNA sequence in accordance with the invention may be selected from the group consisting of: SEQ ID NO: 23, SEQ ID NO: 26; and SEQ ID NO: 28. Alternatively, a nucleic acid of the invention may comprise a variant of the nucleic acids set out in the group consisting of: SEQ ID NO: 23, SEQ ID NO: 26; and SEQ ID NO: 28. Suitable variants may be defined with reference to the considerations set out elsewhere in this disclosure.

The invention will now be further described with reference to the following Examples.

EXAMPLES

Example 1. Protein Characterisation by Expression and Purification of the CBD of Gelatinase A (MMP-2) in Shuffle Cells Shuffle T7 express cells (C3029H, NEB) were transformed with a plasmid encoding for the collagen binding domain (CBD) of gelatinase A (MMP-2), carrying a His6-SUMO tag. The cells were grown in LB at 37° C. and induced with 600 μM IPTG overnight at 18° C. (optimized conditions) and the cleared lysate was purified using a Nickel column (His Trap). The eluted fractions were pooled and the tag was removed by cleaving with a His-tagged SUMO protease overnight at 4° C. Finally, the mixture was then passed back down the Nickel column and the protein collected in the flowthrough, while the protease and the tags were in the elution fraction. The protein identity was verified by mass spectrometry. The levels of expression and purity of the expressed protein were analysed by sodium dodecyl sulphate-polyacrylamide gel electrophoresis (SDS-PAGE) using 15% polyacrylamide gels in a Bio-Rad gel electrophoresis system. In FIG. 1A, lanes 1-5 shows the eluted fractions (pooled), lanes 6 and 7 show the fractions after the tag was removed by cleaving with a His-tagged SUMO protease overnight at 4° C. (precipitate), lane 8 shows the protein collected flow through produced after the mixtures were passed down the Nickel column, and lane 9 the protease and tags from the elution column.

FIG. 1B shows an SDS PAGE gel of the native CBD following a step elution on an anion-exchange column. The protein sample was desalted and applied to a 5 mL Q FF column equilibrated in 20 mM Tris, 10 mM NaCl at pH 8. The protein was shown to be specifically eluted at a concentration of 24% Buffer B, yielding a purity of around 90%, from the fractions 3-13.

Example 2. Binding of CBD of MMP-2 to Gelatin

Figure 2:
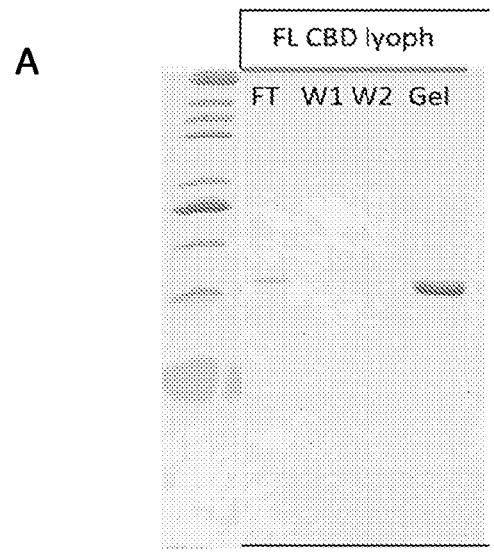
FIG. 2 demonstrates the ability of CBD of MMP-2 to bind to gelatin sepharose, shown qualitatively on an SDS-PAGE gel (panel A). It also shows a diagrammatic representation of the binding assay used and an example of one of the binding curves produced for CBD of MMP-2 binding to type II collagen gelatin.
Figure 2:
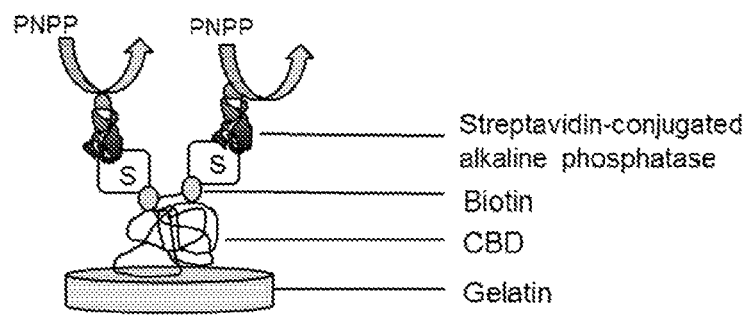
Figure 2:
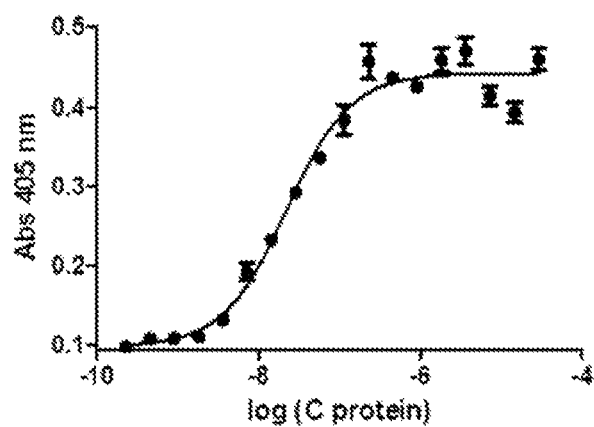

The functionality of the protein was first assessed qualitatively by determining its ability to bind to gelatin sepharose. FIG. 2A shows, results of the loaded sample allowed to bind for 1 minute before collecting the flowthrough (FT). The resin was washed twice (W1 and W2) and then directly resuspended in loading buffer, boiled and loaded on the gel (Gel, Gelatin-bound protein). It was found that most of the protein was bound to the resin.

The inventors also conducted a more quantitative binding assay using type II gelatin coated plates. As described in more detail in the materials and methods section, the proteins were first biotinylated before being added over a concentration range on gelatin-coated plates. The ability of alkaline phosphatase-streptavidin to convert its substrate, p-nitrophenyl phosphate (PNPP), into a coloured product was measured at 405 nm, and used as an indirect indication of the amount of protein bound to gelatin. The specificity of the signal was demonstrated by the fact that a reduced and alkylated version of the CBD did not show any binding (not shown), highlighting the need of the six disulfide bonds for the correct function of the protein. An example of one of the binding curves is shown on the right. Error bars represent standard deviations of three replicates. The CBD was shown to bind with a Kd of 20.4±2.31 nM (Kd±SEM, n=4) shown in FIG. 2B.

Example 3. Binding of Individual Modules of CBD of Gelatinase A to Gelatin

Figure 3:
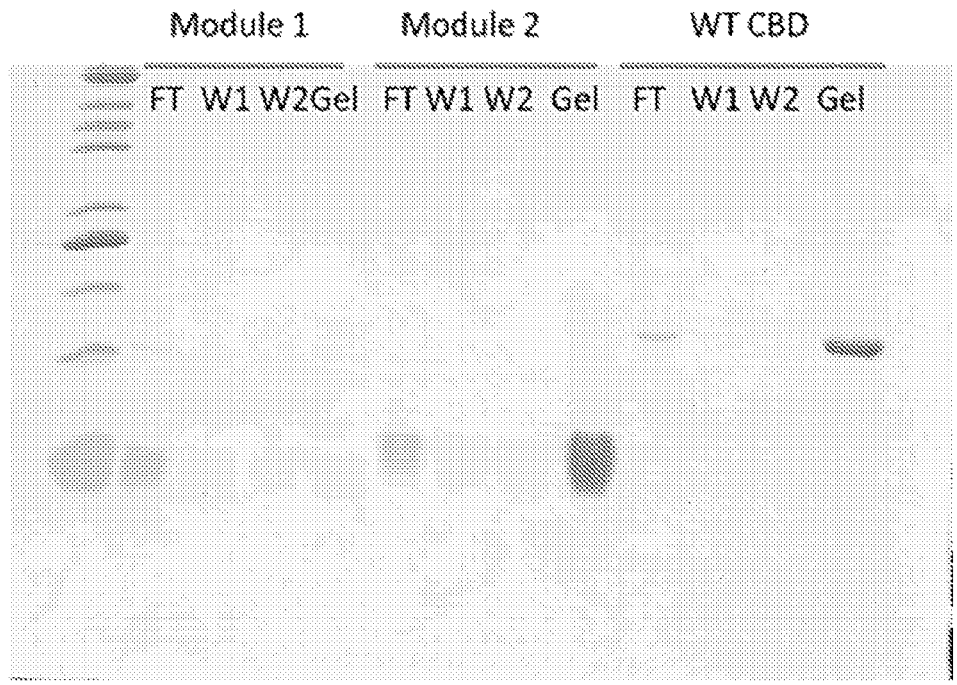
FIG. 3 shows the binding of individual modules (modules 1, 2 and 3) of the CBD of MMP-2 to gelatin sepharose. Shown on an SDS-PAGE gel
Figure 3:

The inventors assessed the ability of the modules (1, 2 and 3) of the CBD of gelatinase A to bind to gelatin. They found that modules 1 and 2 were able to bind to the gelatin sepharose resin, module 1 did not bind. FIG. 3 shows SDS-PAGE gels of each of the modules. The initial samples were loaded and allowed to bind for 1 minute before collecting the flowthrough (FT). The resin was washed twice (W1 and W2) and then directly resuspended in SDS loading buffer, boiled and loaded on the gel (Gel, Gelatin-bound protein).

Figure 4:
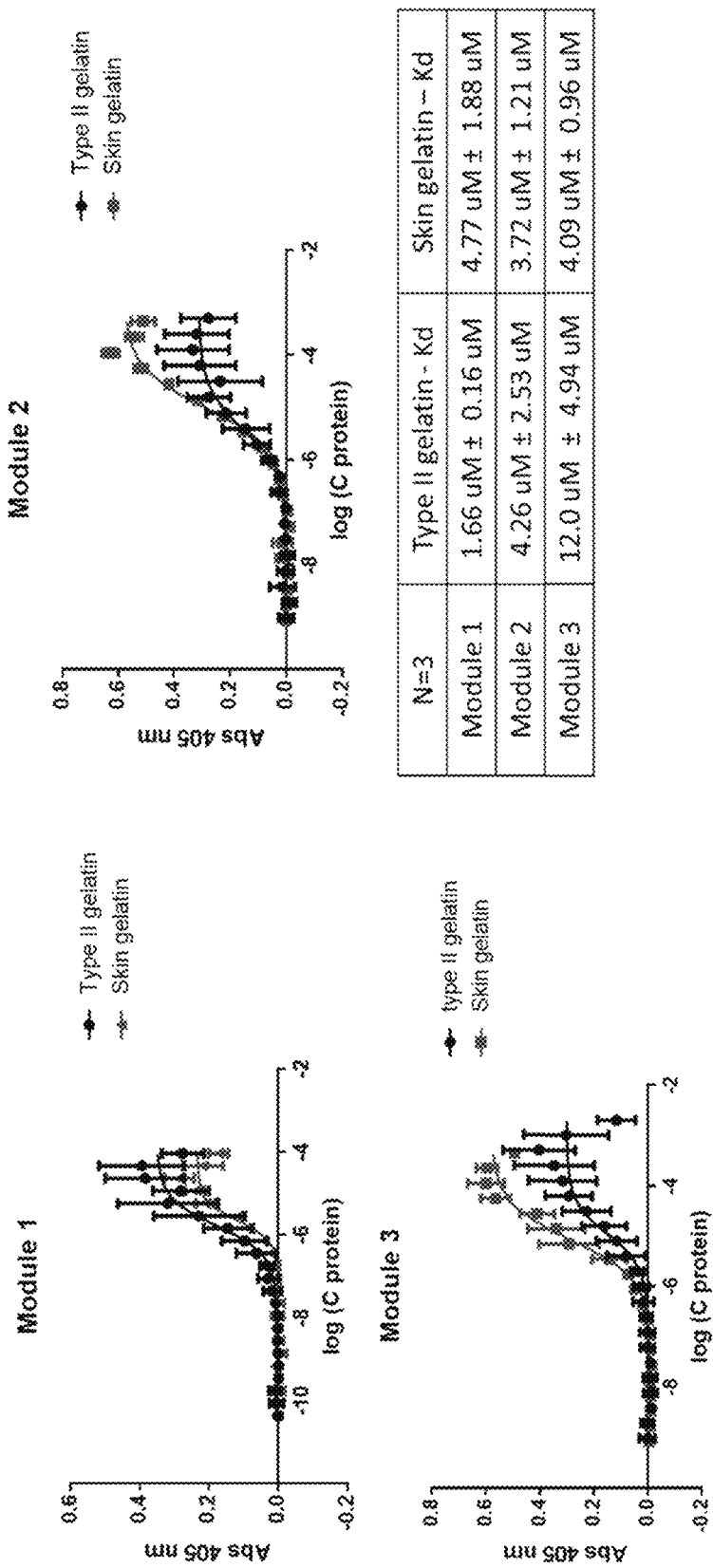
FIG. 4 shows the binding curves of individual modules (modules 1, 2 and 3) of the CBD of MMP-2 to type II collagen gelatin and type I collagen gelatin.

The inventors also conducted a more quantitative binding assay in order to quantify binding affinity (measured as, Kd (nM)) of the individual modules for type II and skin gelatin (type I gelatin). The binding curves are presented in FIG. 4 and the apparent Kd (nM) is shown in Table 2. It was shown that module 1 binds approximatively three times better to type II than type I (skin) gelatin, while module 3 binds three times better to type I (skin) gelatin compared to type II gelatin. Altogether, these data suggested that module 1 could be specific for binding to type II gelatin, while module 3 would bind more preferentially to type I gelatin. Module 2 binds well to both to type I (skin) gelatin and to type II gelatin. The table presents the average Kd±SEM. Error bars on curves represent standard deviations of three replicates.

Example 4. Binding of Individual Modules to Type II Gelatin Demonstrated by NMR The inventors verified the specificity of binding of individual modules within the full-length CBD. The binding of the peptide to type II gelatin (heat-denatured collagen) was studied by NMR. 8 spectra of the free peptide at 100 μM in 25 mM Sodium phosphate buffer, pH 6.5 were acquired with a 800 kHz Bruker spectrometer before adding the ligand at a 40:1 (peptide:gelatin) ratio.

Disappearing peaks were observed following the addition of the ligand, indicating their involvement in the binding to type II gelatin. When the assignments published by Xu et al., (2009) were reported onto our spectrum, the residues involved in the binding were found to belong to module 2 (table 3). This finding was confirmed by mapping the peaks onto the PBD structure of the CBD of MMP-2 (data not shown).

When a higher amount of type II gelatin was added (ratio peptide:gelatin of 1.5:1), it was observed that peaks from module 1 also broadened, while those from module 3 were only minimally shifted, an observation which confirms the inventors' hypothesis that module 1 would be specifically binding to type II gelatin. Its ability to bind to type II gelatin was confirmed by NMR (data not shown) and the residues identified were mapped to the binding site of the module (data not shown).

NMR peaks from module 3 shifted only minimally, indicating that module 3 does not bind well to type II gelatin. Most of the peaks from both modules 2 and 1 disappeared, indicating that module 1 may have a higher affinity for type II gelatin than module 3 (data not shown).

Overlay of the spectra from the free module 1 and the module 1 plus gelatin complex was obtained. The residues which bind belong to the binding site of module 1 (residues shown in Table 3).

Example 5. Generation of Peptides Comprising a Plurality of Modules Corresponding to Module 1, Module 2, or Module 3 of the CBD of MMP-2

Figure 5:
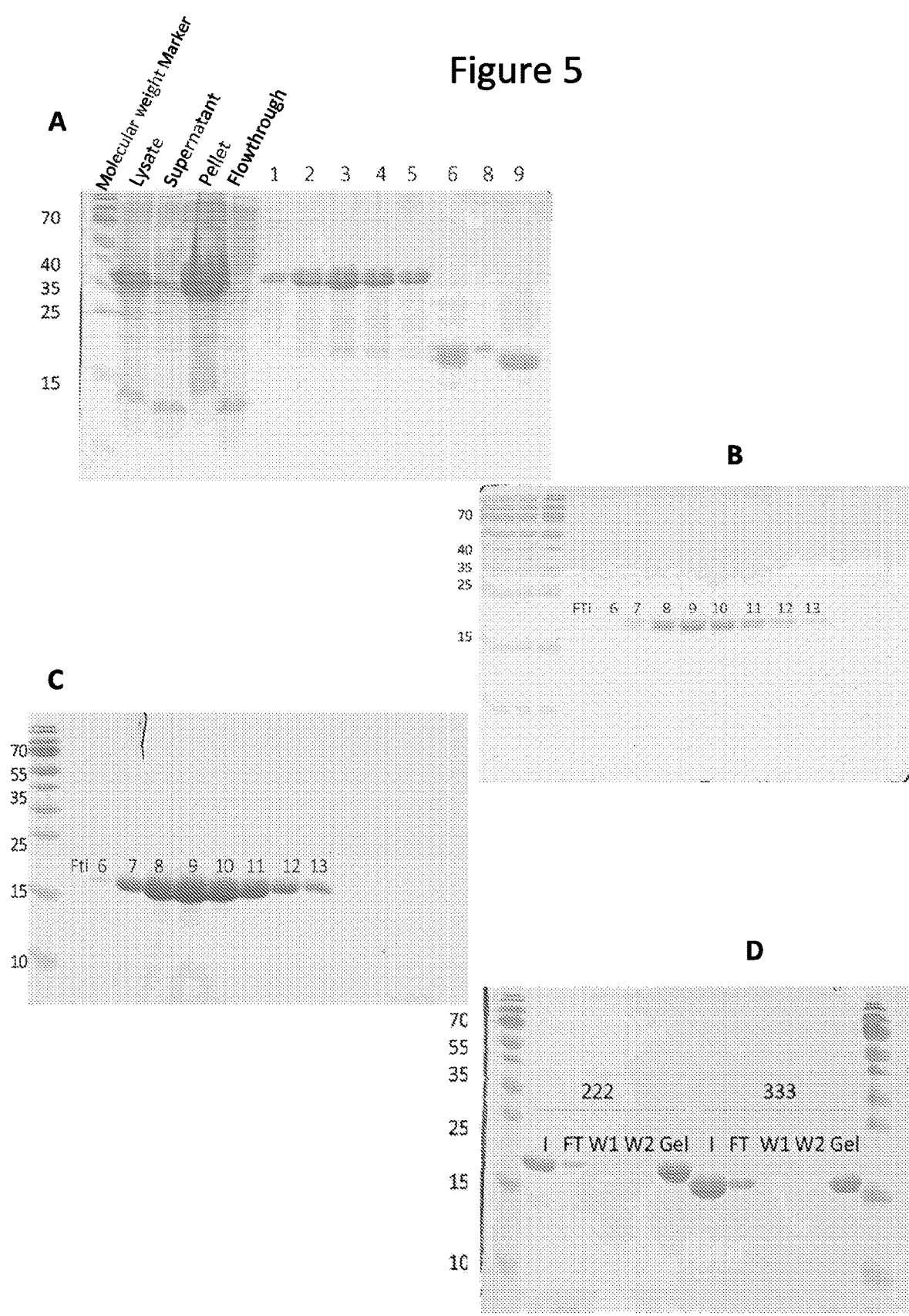
FIG. 5 shows SDS-PAGE gels demonstrating the expression and purification of a peptide comprising three modules corresponding to module 2 of the CBD of MMP-2 (222) and a peptide comprising three modules corresponding to module 3 of the CBD of MMP-2 (333) in Shuffle cells.

The inventors generated chimeric peptides comprising three modules corresponding to module 1 (111), three modules corresponding to module 2 (222) and three modules corresponding to module 3 (333) of the CBD of MMP-2. Both 222 and 333 were expressed in Shuffle cells, and purified as described in the materials and methods section Shown in FIG. 5 A-C.

FIG. 5A shows an SDS PAGE gels showing the expression of the SUMO-222. Shuffle T7 express cells (C3029H, NEB) were transformed with the plasmid encoding for the corresponding peptide carrying a His6-SUMO tag. The cells were grown in LB at 37° C. and induced with IPTG overnight at 18° C. (optimized conditions) and the cleared lysate was purified using a Nickel column (His Trap). The eluted fractions (lanes 1-5) were pooled and the tag was removed by cleaving with a His-tagged SUMO protease overnight at 4° C. (Lane 6) Finally, the mixture was then passed back down the Nickel column and the peptide collected in the flowthrough (lane 8), while the protease and the tags were in the elution fraction (Lane 9).

FIG. 5B shows SDS PAGE gel of the 222, and 5C shows an SDS-PAGE gel of 333, both (222 and 333) following their elution off an anion-exchange column. The peptide samples were desalted and applied to a 5 mL Q FF column equilibrated in 20 mM Tris, 10 mM NaCl at pH 8.0. The peptides were eluted with a linear gradient of buffer B, yielding a purity of around 90%. No peptide was lost in the flowthrough (FTi).

FIG. 5D shows qualitative binding of 222 and 333 assessed on a gelatin sepharose column. The initial sample (I) was loaded and allowed to bind for 1 minute before collecting the flowthrough (FT). The resin was washed twice (W1 and W2) and then directly resuspended in Loading buffer, boiled and loaded on the gel (Gel, Gelatin-bound peptide).

The peptide comprising 111 was found in the insoluble fraction (data not shown). No free cysteines were present in 222 or 333 according to a DTNB assay (data not shown) and both peptides were able to bind to the gelatin sepharose resin.

Figure 6:
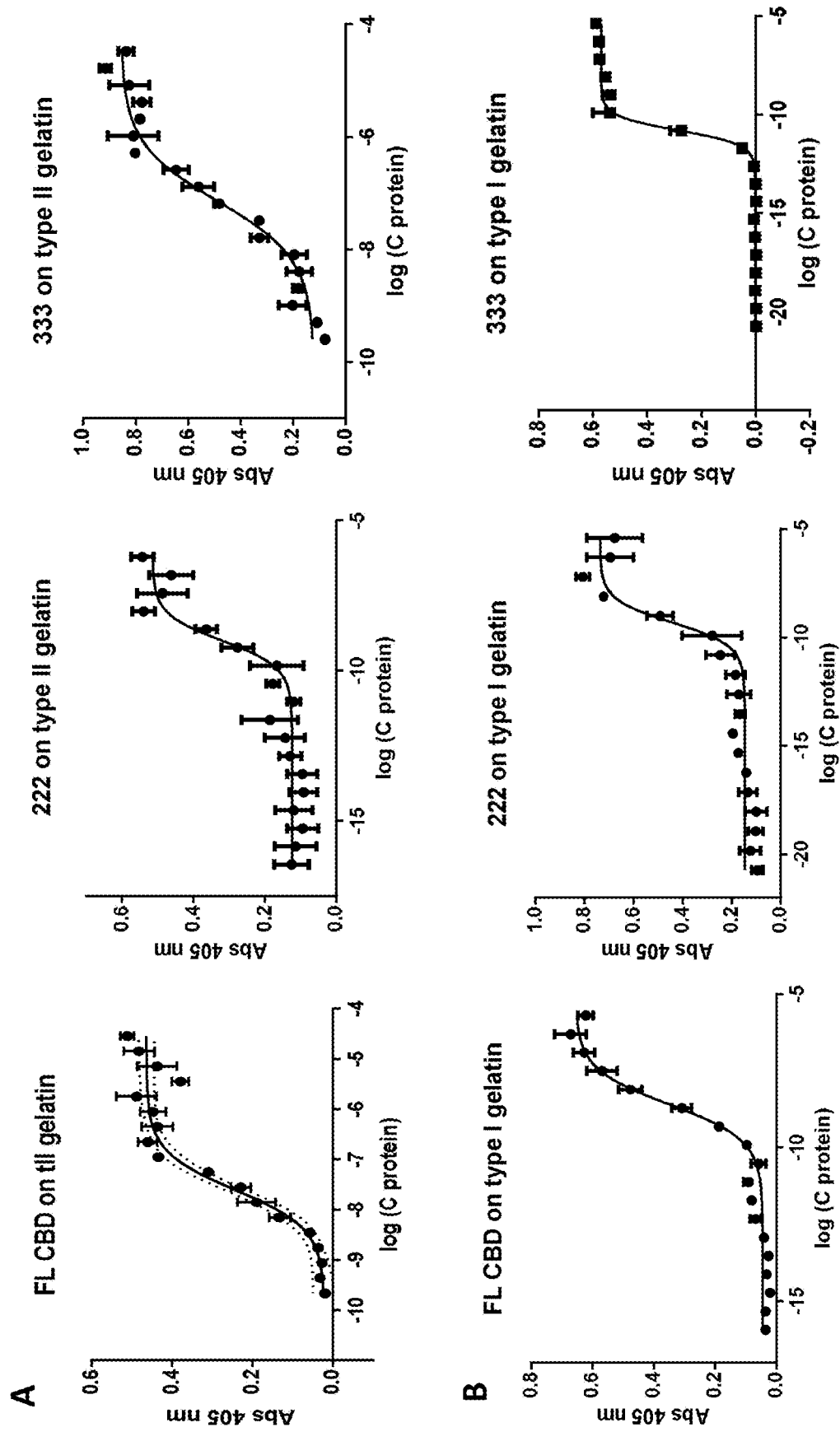
FIG. 6 shows the binding curves of full length CBD (FL CBD) of MMP-2 and a peptide comprising three modules corresponding to module 2 of the CBD of MMP-2 (222) and a peptide comprising three modules corresponding to module 3 of the CBD of MMP-2 (333) to type II collagen gelatin and type I collagen gelatin.

Example 6. Binding of Chimeric Peptides Comprising Three Modules Corresponding to Module 2 (222) and Three Modules Corresponding to Module 3 (333) to Type I and Type II Gelatin The chimeric peptides were assessed for binding to collagen type I and type II gelatin using the plate binding assay (described in the materials and methods section). FIG. 6A shows the results of the binding assay of the full length CBD of MMP-2, and peptides of the invention 222 and 333 (respectively comprising three modules corresponding to module 2 and module 3 of the CBD of MMP-2) investigating binding to collagen type II gelatin (panel A) and collagen type I gelatin (panel B). The data show that 333 binds with a much tighter affinity to type I than type II gelatin. The binding affinities of the peptides are shown in Table 1. 333 binds to collagen type I gelatin with a binding affinity of 0.0159 Kd (nM), a higher affinity than the full length CBD of MMP-2, which binds to collage type I gelatin at an affinity of 2.58 Kd (nM). Interestingly, 222 binds to type II gelatin, (1.46 Kd (nM)) with a 10-fold higher affinity than the full length CBD (20.4 Kd (nM)). Surprisingly, the binding affinity of 222 to type II collagen gelatin was found to be 10 times higher than that of 333. A peptide comprising three modules corresponding to module 1 was not tested.

Example 7. MSC Coating with Peptide Comprising Three Modules Corresponding to Module 2 of the CBD of MMP-2 (222)

The inventors surrounded the peptide with a surfactant corona, enabling the peptide to be incorporated into the membrane of stem cells. The peptide modification is a two-step process, with an initial cationisation following the surfactant addition. The cationisation involves the covalent coupling of N,N'-dimethyl-1,3-propanediamine (DMPA) to the carboxylic residues of the peptide. Following covalent coupling with DMPA, the cationised peptide is then enabled to interact electrostatically with the negatively charged surfactant glycolic acid ethoxylate 4-nonylphenyl ether. This surfactant results from the oxidation of Igepal CO-890 (described in more detail in the materials and methods section).

Dynamic Light scattering was used to measure both the hydrodynamic radius and the zeta potential of a peptide. The measurements confirm that the two-step conjugation process was successful, as presented in table 4. The caitonisation induced an increase in the charge of the peptide and a small increase in its hydrodynamic radius. The latter was further increased following the addition of the surfactant, confirming the creation of the corona surrounding the peptide. The surfactant addition also enabled the neutralization of the charge.

Figure 7A:
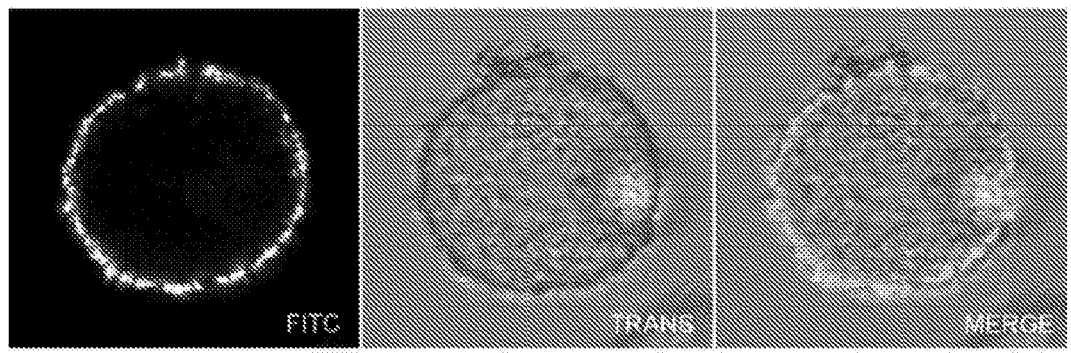
FIG. 7 shows a confocal image demonstrating the coating of MSCs with Surfactant-FTIC and a peptide comprising three modules corresponding to module 2 of the CBD of MMP-2 (222) (panel A). It also shows a confocal image of the coated MSCs labelled with membrane dye FM-4-64 (panel B).

One million mesenchymal stem cells were initially treated with 300 µL of 5 µM Surfactant-FITC-222 for 30 minutes at 37° C. Cells were then washed with heparin ammonium salt, plated and imaged with a confocal microscope. FIG. 7A shows that the MSCs were successfully coated with 222.

Figure 7B:
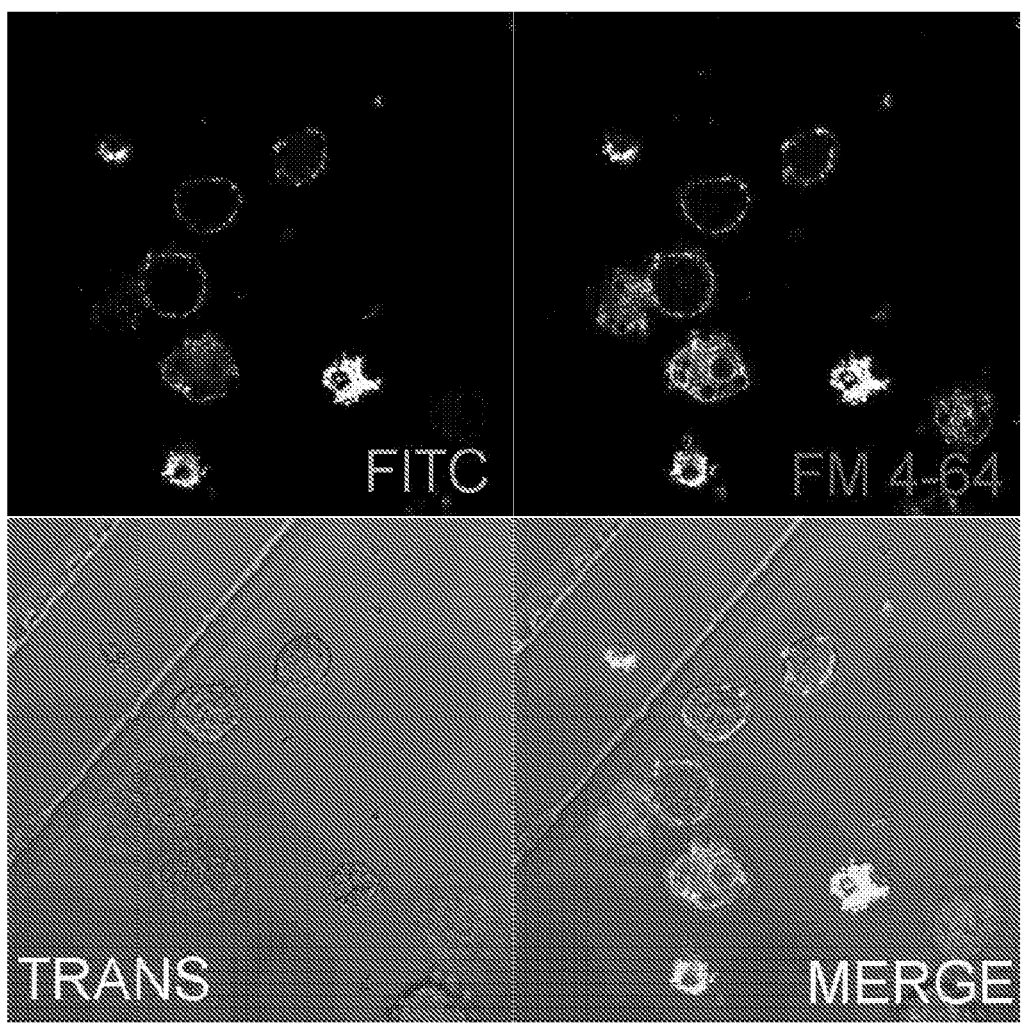

FIG. 7B shows confocal images showing 222 being co-localised with the membrane dye FM-4-64. Some cells showed an internalisation of the dye, an indication of cell death (probably because late passage cells were being used for this set of experiments). The toxicity of the coating process was tested with a trypan-blue viability assay. There was no difference in cells viability when treated cells were compared with untreated controls, showing that the coating was not toxic.

Example 8. Binding of a Conjugate of the Invention to Denatured Type II Collagen The inventors have demonstrated that a conjugate according to the second or sixth aspects of the invention comprising an MSC payload and a chimeric peptide comprising three modules corresponding to module 2 (222, SEQ ID NO: 25) binds with high affinity to denatured type II collagen. Coating MSCs with 222 resulted in an increase in attachment of the coated MSCs to type II collagen gelatin. The inventors compared the ability of a conjugate of the invention (comprising MSCs and 222) and uncoated control MSCs to bind to type II collagen gelatin or to plastic after 24 h of culture.

The conjugates were made by coating MSCs with 5 μM of 222. After washing in 0.04 mg/mL heparin ammonium salt (Sigma, H6279-25 KU) in PBS (Sigma, D8537), MSCs were resuspended in low glucose (1000 mg/dm3) DMEM (Sigma, D5546) with 100 units/ml penicillin, 100 μg/mL streptomycin (Sigma, P0781), 2 mM GlutaMAX supplement (Gibco, 35050-038) at a density of 4.000.000 cells/mL. The conjugates and the control MSCs (uncoated) were seeded on multi-well plastic tissue culture plates that were either uncoated or coated with collagen type II gelatin (0.5 μg type II gelatin/well). 200 μL of conjugate or control MSCs were added in the first two rows of wells, before performing serial 1 in 2 dilutions across the plates. Control MSCs were used at the same final cell dilutions as the conjugate (222-coated MSCs). The tissue culture plates were incubated for 24 hours at 37 degrees, 5% CO2 and then washed once with phenol-free, low glucose (1000 mg/dm3) DMEM (D5921), before adding 100 μL of this medium containing the dye FM 4-64 (100 μL/mL), which stains the cell membranes with a red fluorescent probe. Images of the conjugates and uncoated MSCs were obtained using an epifluorescent microscope.

Figure 10:
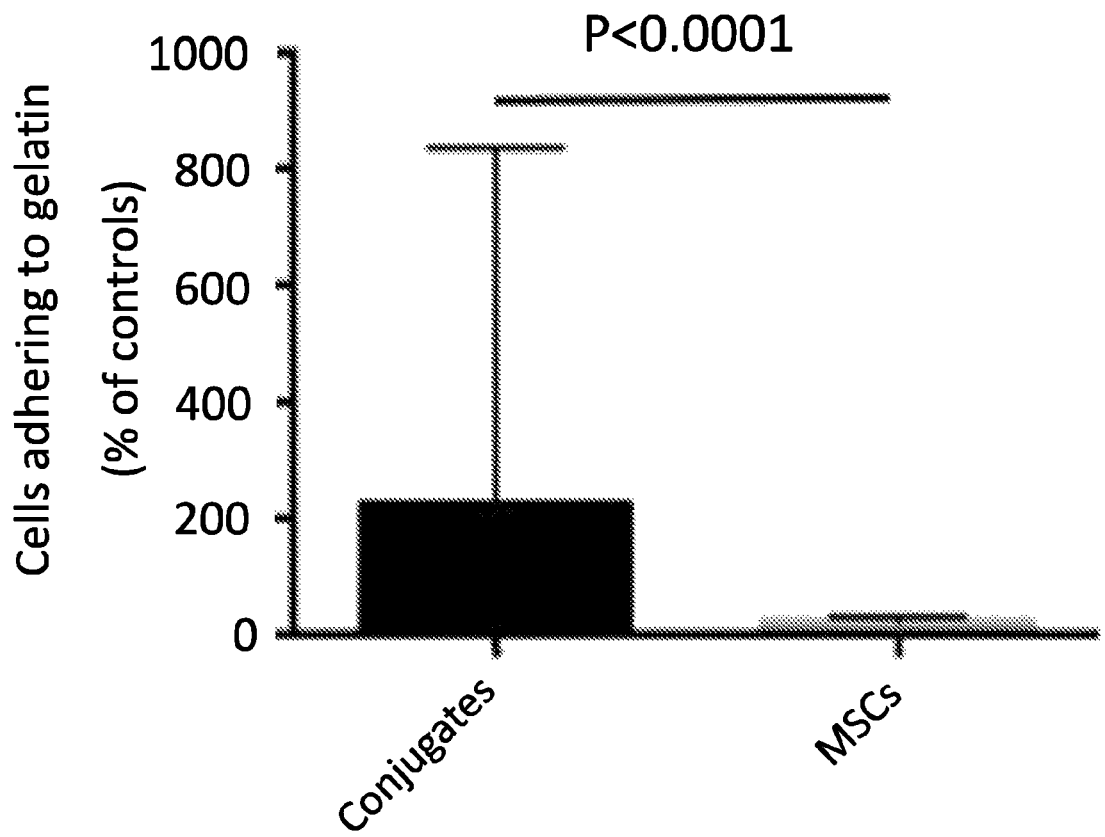
FIG. 10 shows a quantitative analysis of binding of conjugates of the invention (comprising MSCs and the peptide of the invention 222) or unconjugated control MSCs to type II collagen gelatin. The bars show binding to type II collagen gelatin as a percentage of binding to plastic (control). Results are the median (interquartile range) for n=64 image locations in the culture wells.

Computer images of the stained cells were then mapped into 16 squares to overlay the wells of the tissue culture plates, the number of cells attached to type II collagen gelatin or to plastic were counted in each of these squares. The cells attached to gelatin were then calculated as a percentage of the cells attached to plastic in the same square of the equivalent well on control plates. The results of this comparison are shown in FIG. 10.

Figure 8:
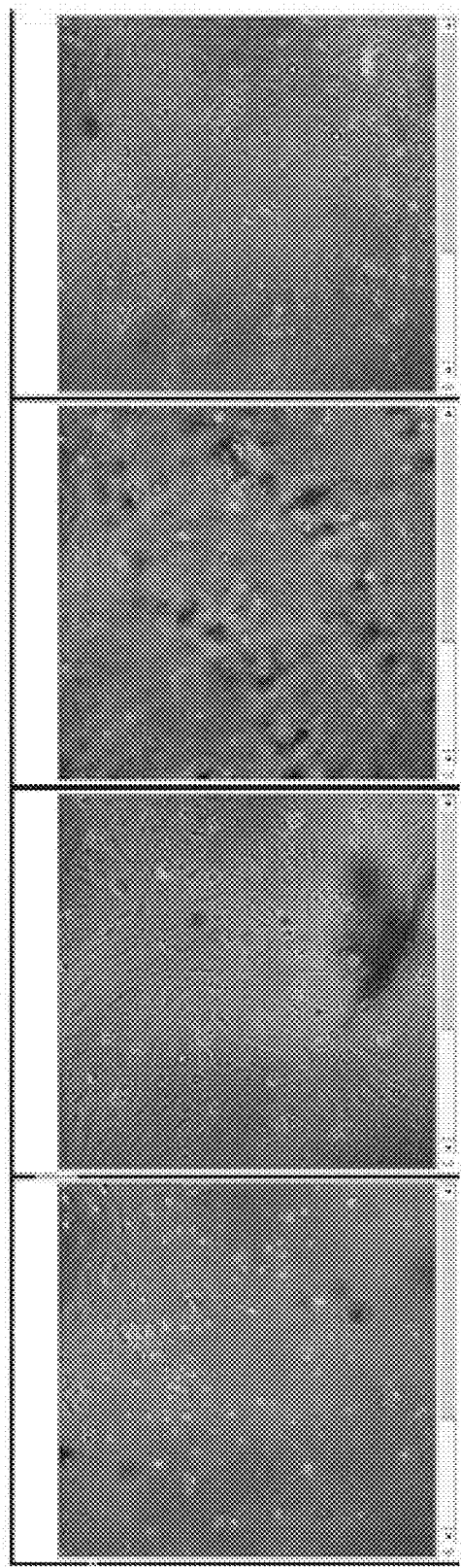
FIG. 8 shows binding of uncoated control MSCs incubated on plastic (Panel A) or on type II collagen gelatin (Panel B). Images were captured by epifluorescent microscopy. Cells were cultured for 24 hours before staining with FM 4-64. Images were then captured by epifluorescent microscopy.
Figure 8:
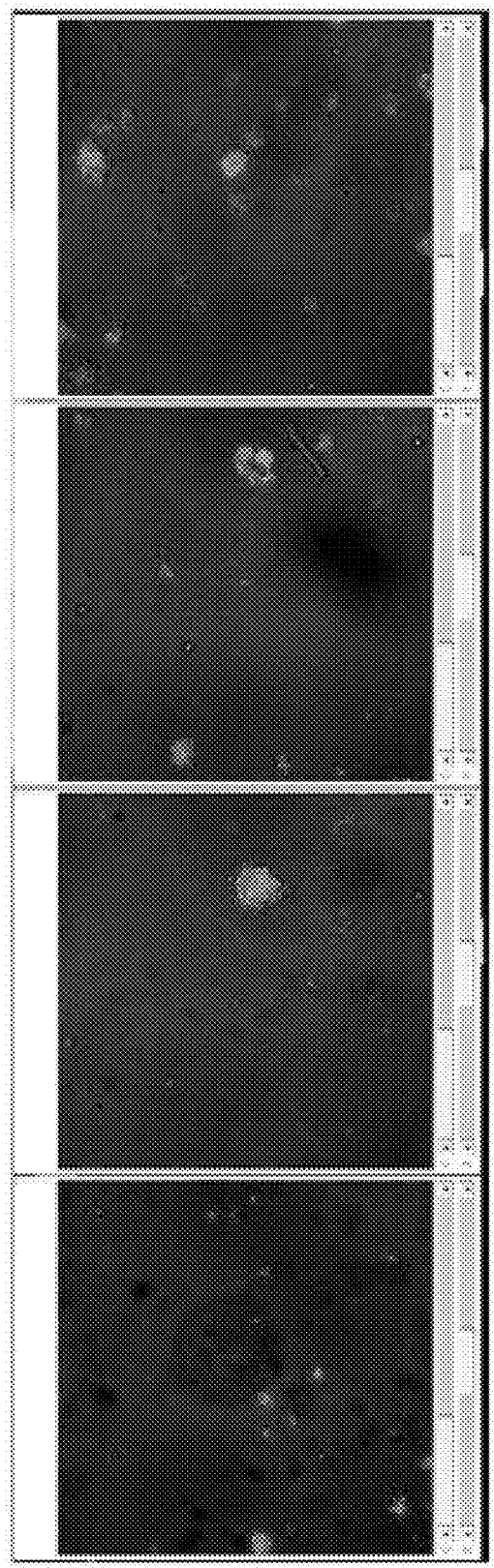
Figure 9:
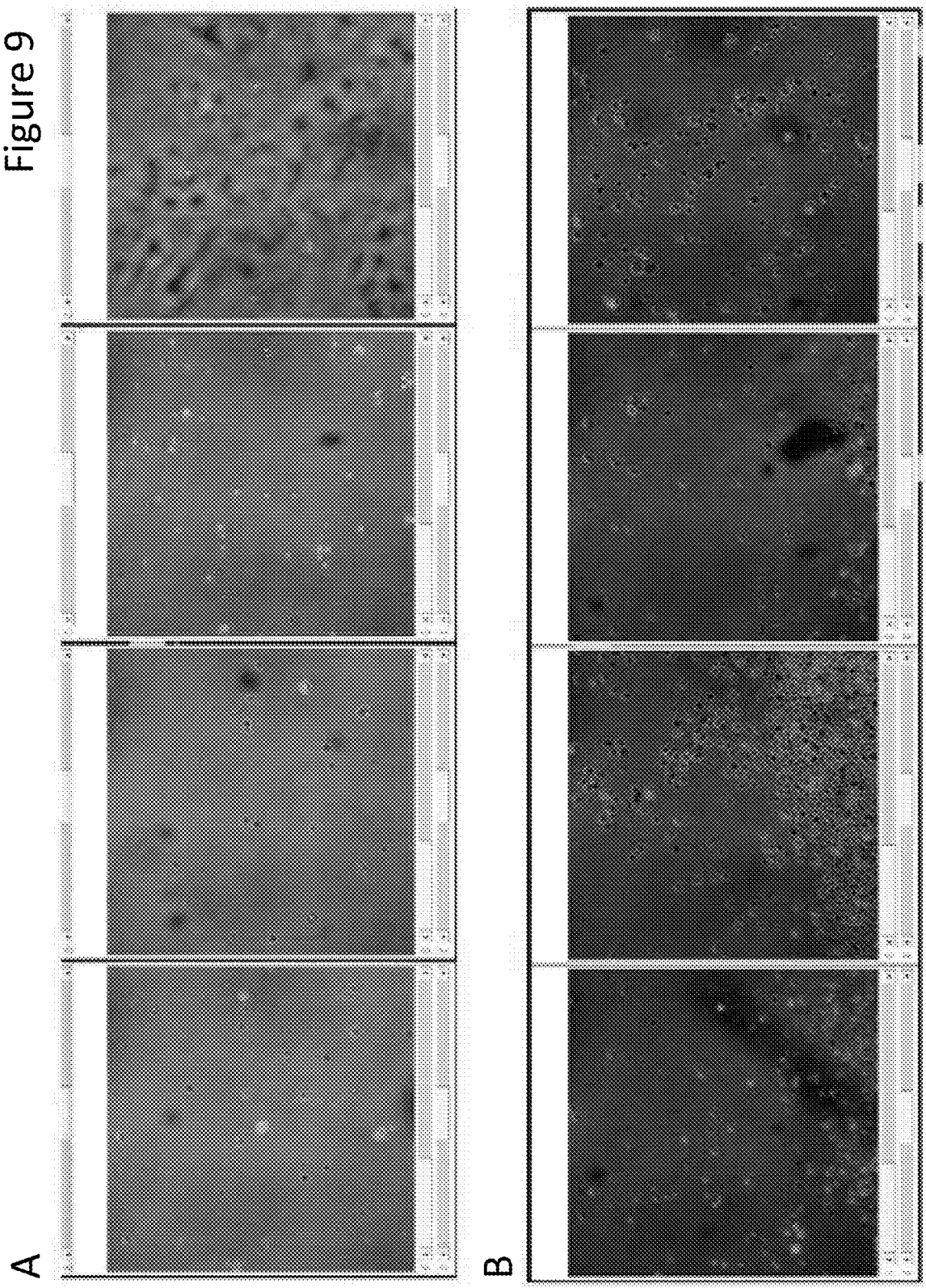
FIG. 9 shows the binding of conjugates of the invention (comprising MSCs and the peptide of the invention, 222) incubated on plastic (Panel A) or on type II collagen gelatin (Panel B). Cells were cultured for 24 hours before staining with FM 4-64. Images were then captured by epifluorescent microscopy.

Epifluorescent images from one of the four replicate experiments conducted are shown in FIGS. 8 and 9. Results are shown for the lowest dilution wells (25,000 per well) as cells in these wells were clearly visible under the microscope. The images shown are typical results from the four replicate experiments. FIG. 8 shows the binding of control MSCs to plastic (uncoated tissue culture plates) (FIG. 8A) and to type II collagen gelatin (coated tissue culture plates) (FIG. 8B). FIG. 8 illustrates that the control MSCs clearly bind more effectively to plastic than to type II collagen gelatin. This would appear to be the result of non-specific binding.

FIG. 9 shows the binding of the conjugate of the invention (MSCs coated with 222) to plastic (FIG. 9A) and to type II collagen gelatin (FIG. 9B). The conjugate clearly binds more effectively to type II collagen gelatin than to plastic. The percentage of conjugates or control MSCs bound to collagen type II gelatin (as compared to the numbers of the conjugates or control cells bound to plastic) was calculated. This was calculated for each of the 16 wells in the 4 replicate experiments (n=64 in each group). FIG. 10 shows the percentage of conjugates of the invention (MSCs coated with 222) that bound to type II collagen gelatin relative to binding to plastic, and also the percentage of control MSCs that bound to collagen type II gelatin relative to binding to plastic. As shown in FIG. 10, the binding of 222-coated MSCs to gelatin relative to plastic was significantly higher than that of the control MSCs. The median % adhesion of 222-coated MSCs was 224.4% (range=31.6%-5,160%) relative to plastic, whereas the median % adhesion of control MSCs was 23.67% (range=25.6%-78.4%).

The finding that a conjugate of the invention is more effective at binding to type II collagen gelatin than to plastic is consistent with the finding that 222 has a very high affinity for gelatin (and particularly type II collagen gelatin).

Surprisingly, the inventors have shown that not only was there a larger number of conjugates bound to type II collagen gelatin than control MSCs (compare FIG. 9B with 8B) but also there were very few conjugates bound to plastic compared with the large number of control MSCs bound to plastic (compare FIG. 1B with 1A). This suggests that coating MSCs with 222 to form a conjugate reduces the non-specific binding of the cell membrane to plastic, possibly by blocking the interactions between the cell and tissue culture material.

The findings of this study provide direct support for the utility of a conjugate of the invention comprising an MSC payload and a chimeric peptide comprising three modules corresponding to module 2 (222) in prevention and/or treatment of a disorder associated with generation or accumulation of gelatin. It will be appreciated that type II collagen gelatin is found at the articular surface in osteoarthritic joints (Hollander et. al, "Damage to type II collagen in aging and osteoarthritis starts at the articular surface, originates around chondrocytes, and extends into the cartilage with progressive degeneration" J Clin Invest. 1995 December; 96(6): 2859-69), and that MSCs may provide useful therapeutic agents for use in the treatment of this disease.

SEQUENCE INFORMATION

Amino acid sequence of full length MMP-2

SEQ ID NO: 1

```
MEALMARGAL TGPLRALCLL GCLLSHAAAA PSPIIKFPGD VAPKTDKELA VQYLNTFYGC

PKESCNLFVL KDTLKKMQKF FGLPQTGDLD QNTIETMRKP RCGNPDVANY NFFPRKPKWD

KNQITYRIIG YTPDLDPETV DDAFARAFQV WSDVTPLRFS RIHDGEADIM INFGRWEHGD

GYPFDGKDGL LAHAFAPGTG VGGDSHFDDD ELWTLGEGQV VRVKYGNADG EYCKFPFLFN

GKEYNSCTDT GRSDGFLWCS TTYNFEKDGK YGFCPHEALF TMGGNAEGQP CKFPFRFQGT

SYDSCTTEGR TDGYRWCGTT EDYDRDKKYG FCPETAMSTV GGNSEGAPCV FPFTFLGNKY

ESCTSAGRSD GKMWCATTAN YDDDRKWGFC PDQGYSLFLV AAHEFGHAMG LEHSQDPGAL

MAPIYTYTKN FRLSQDDIKG IQELYGASPD IDLGTGPTPT LGPVTPEICK QDIVFDGIAQ

IRGEIFFFKD RFIWRTVTPR DKPMGPLLVA TFWPELPEKI DAVYEAPQEE KAVFFAGNEY

WIYSASTLER GYPKPLTSLG LPPDVQRVDA AFNWSKNKKT YIFAGDKFWR YNEVKKKMDP

GFPKLIADAW NAIPDNLDAV VDLQGGGHSY FFKGAYYLKL ENQSLKSVKF GSIKSDWLGC
```

Amino acid sequence of CBD of MMP-2
SEQ ID NO: 2
ADGEYCKFPPLFNGKEYNSCTDTGRSDGFLWCSTTYNFEKDGKYGFCPHEALFTMGGNA

EGQPCKFPFRFQGTSYDSCTTEGRTDGYRWCGTTEDYDRDKKYGFCPETAMSTVGGNSE

GAPCVFPFTFLGNKYESCTSAGRSDGKMWCATTANYDDDRKWGFCPD

Amino acid sequence of peptide comprising the CBD of MMP-2. The residues that are not underlined constitute the CBD. The underlined residues may optionally be added to assist expression of the sequence.
SEQ ID NO: 3
<u>RVKYGN</u>ADGEYCKFPPLFNGKEYNSCTDTGRSDGFLWCSTTYNFEKDGKYGFCPHEALFT

MGGNAEGQPCKFPFRFQGTSYDSCTTEGRTDGYRWCGTTEDYDRDKKYGFCPETAMST

VGGNSEGAPCVFPFTFLGNKYESCTSAGRSDGKMWCATTANYDDDRKWGFCPD<u>QGYS</u>

DNA sequence encoding the CBD of MMP-2
SEQ ID NO: 4
cgtgtgaaatatggtaatgccgatggcgaatattgcaaatttccgtttctgtttaacggcaaagagtataatagctgtaccgataccg gtcgtagtgatggttttctgtggtgtagcaccacctataactttgagaaagatggcaaatatggcttttgtccgcatgaagcactgttta ccatgggtggtaatgcggaaggtcagccgtgtaaatttccttttcgctttcagggcaccagctatgatagttgtaccaccgaaggtc gtaccgatggttatcgttggtgcggtacaaccgaagattatgatcgtgacaaaaaatacggtttctgtccggaaaccgcaatgag caccgttggtggtaatagtgaaggtgcaccgtgtgtttttcctttacctttctgggtaacaaatatgaaagctgtaccagtgcaggtc gttcagatggtaaaatgtggtgcgcaaccaccgcaaattatgatgatgatcgtaaatggggttttttgcccagatcagggttatagc DNA sequence encoding the CBD of MMP-2 (with stop codon)
SEQ ID NO: 5
Cgtgtgaaatatggtaatgccgatggcgaatattgcaaatttccgtttctgtttaacggcaaagagtataatagctgtaccgatacc ggtcgtagtgatggttttctgtggtgtagcaccacctataactttgagaaagatggcaaatatggcttttgtccgcatgaagcactgttt accatgggtggtaatgcggaaggtcagccgtgtaaatttccttttcgctttcagggcaccagctatgatagttgtaccaccgaaggt cgtaccgatggttatcgttggtgcggtacaaccgaagattatgatcgtgacaaaaaatacggtttctgtccggaaaccgcaatga gcaccgttggtggtaatagtgaaggtgcaccgtgtgthttccgtttacctttctgggtaacaaatatgaaagctgtaccagtgcaggt cgttcagatggtaaaatgtggtgcgcaaccaccgcaaattatgatgatgatcgtaaatggggttttttgcccagatcagggttatagc taa Amino acid sequence of module 1 of CBD of MMP-2
SEQ ID NO: 6
ADGEYCKFPPLFNGKEYNSCTDTGRSDGFLWCSTTYNFEKDGKYGFCPH Amino acid sequence comprising module 1 of the CBD of MMP-2. The residues that are not underlined constitute module 1. The underlined residues may optionally be added to assist expression of the sequence.
SEQ ID NO: 7
<u>V K Y G N</u> A D G E Y C K F P P L F N G K E Y N S C T D T G R S D G F L W C S T T Y N F E K D G K Y G F C P H <u>E A L F T M</u>

Amino acid sequence of a variant module corresponding to module 1 of the CBD of MMP-2 (used in exemplary peptide of the invention 111):
SEQ ID NO: 8
VRVKYVNADGEYCKFPPLFNGKEYNSCTDTGRSDGFLWCSTTYNFEKDGKYGFC

P

DNA sequence encoding an amino acid sequence comprising module 1 of the CBD of MMP-2
SEQ ID NO: 9
gtgaaatatggtaatgccgatggcgaatattgcaaatttccgtttctgtttaacggcaaagagtataatagctgtaccgataccggtc gtagtgatggttttctgtggtgtagcaccacctataactttgagaaagatggcaaatatggcttttgtccgcatgaagcactgtttacc atg DNA sequence encoding an amino acid sequence comprising module 1 of the CBD of MMP-2 with stop codon
SEQ ID NO: 10
Gtgaaatatggtaatgccgatggcgaatattgcaaatttccgtttctgtttaacggcaaagagtataatagctgtaccgataccggt cgtagtgatggttttctgtggtgtagcaccacctataactttgagaaagatggcaaatatggcttttgtccgcatgaagcactgtttac catgtaa Amino acid sequence of Module 2 of CBD of MMP-2
SEQ ID NO: 11
AEGQPCKFPFRFQGTSYDSCTTEGRTDGYRWCGTTEDYDRDKKYGFCPE Amino acid sequence comprising module 2 of the CBD of MMP-2. The residues that are not underlined constitute module 2. The underlined residues may optionally be added to assist expression of the sequence.
SEQ ID NO: 12
ALFTMGGNAEG QPCKFPFRFQ GTSYDSCTTE GRTDGYRWCG TTEDYDRDKK

YGFCPETA

Amino acid sequence of a variant module corresponding to of module 2 of the CBD of MMP-2
SEQ ID NO: 13
VFTMYGNAEG QPCKFPFRFQ GTSYDSCTTE GRTDGYRWCG TTEDYDRDKK YGFCP Amino acid sequence of a variant module corresponding to module 2 of the CBD of MMP-2 (used in exemplary peptide of the invention 222)
SEQ ID NO: 14
LFTMGGNAEGQPCKFPFRFQGTSYDSCTTEGRTDGYRWCGTTEDYDRDKKYGFC

P

DNA sequence encoding a peptide comprising a variant module corresponding to module 2 of the CBD of MMP-2
SEQ ID NO: 15
gcactgtttaccatgggtggtaatgcggaaggtcagccgtgtaaatttccttttcgctttcagggcaccagctatgatagttgtaccac cgaaggtcgtaccgatggttatcgttggtgcggtacaaccgaagattatgatcgtgacaaaaaatacggtttctgtccggaaacc gca DNA sequence encoding a peptide comprising a module corresponding to module 2 of the CBD of MMP-2 with stop codon
SEQ ID NO: 16
gcactgtttaccatgggtggtaatgcggaaggtcagccgtgtaaatttccttttcgctttcagggcaccagctatgatagttgtaccac cgaaggtcgtaccgatggttatcgttggtgcggtacaaccgaagattatgatcgtgacaaaaaatacggtttctgtccggaaacc gcataa Amino acid sequence of Module 3 of CBD of MMP-2
SEQ ID NO: 17
SEGAPCVFPFTFLGNKYESCTSAGRSDGKMWCATTANYDDDRKWGFCPD Amino acid sequence of a peptide comprising module 3 of the CBD of MMP-2. The residues that are not underlined constitute module3. The underlined residues may optionally be added to assist expression of the sequence.
SEQ ID NO: 18
M S T V G G N S E G A P C V F P F T F L G N K Y E S C T S A G R S D G K M W C A T T

A N Y D D D R K W G F C P D Q G

Amino acid sequence of a variant module corresponding to module 3 of the CBD of MMP-2 (used in exemplary peptide of the invention 333):
SEQ ID NO: 19
MSTVGGNSEGAPCVFPFTFLGNKYESCTSAGRSDGKMWCATTANYDDDRKWGF

CP

DNA encoding a peptide comprising a module corresponding to module 3 of the CBD of MMP-2
SEQ ID NO: 20
Atgagcaccgttggtggtaatagtgaaggtgcaccgtgtgttttccgtttacctttctgggtaacaaatatgaaagctgtaccagtgc aggtcgttcagatggtaaaatgtggtgcgcaaccaccgcaaattatgatgatgatcgtaaatggggttttttgcccagatcagggt DNA encoding a peptide comprising a module corresponding to module 3 of the CBD of MMP-2 with stop codon
SEQ ID NO: 21
Atgagcaccgttggtggtaatagtgaaggtgcaccgtgtgttttccgtttacctttctgggtaacaaatatgaaagctgtaccagtgc aggtcgttcagatggtaaaatgtggtgcgcaaccaccgcaaattatgatgatgatcgtaaatggggttttttgcccagatcagggttaa Exemplary peptide 111 comprising three modules corresponding to module 1 of the CBD of
MMP-2. The Methionine (M) and arginine (R) residues underlined are both included from the
module 2 sequences because they are thought to be important for stabilising the interaction
between module 2 and module 1.

SEQ ID NO: 22

E G Q V V R V K Y G N A D G E Y C K F P F L F N G K E Y N S C T D T G R S D G F L W

C S T T Y N F E K D G K Y G F C P H E A L F V <u>M</u> Y G N A D G E Y C K F P F L F N G K E

Y N S C T D T G R S D G F <u>R</u> W C S T T Y N F E K D G K Y G F C P E T A V R V K Y G N

A D G E Y C K F P F L F N G K E Y N S C T D T G R S D G F L W C S T T Y N F E K D G K

Y G F C P D Q G Y S L

DNA sequence encoding exemplary peptide 111

SEQ ID NO: 23

GAAGGTCAGGTTGTTCGTGTGAAATATGGTAATGCAGATGGCGAGTATTGCAAATTTCC

GTTTCTGTTTAACGGCAAAGAGTATAATAGCTGTACCGATACCGGTCGTAGTGATGGTT

TTCTGTGGTGTAGCACCACCTATAACTTTGAGAAAGATGGCAAATATGGCTTTTGTCCG

CATGAAGCACTGTTTGTGATGTATGGCAATGCCGATGGTGAATACTGTAAATTCCCATTT

CTGTTCAATGGTAAAGAATACAACTCATGCACCGATACAGGCCGTTCAGATGGCTTTCG

TTGGTGTTCAACCACCTACAATTTCGAAAAAGACGGTAAGTATGGTTTCTGTCCGGAAA

CCGCAGTGCGCGTTAAATATGGCAACGCGGACGGGGAATATTGTAAGTTTCCGTTCTTA

TTCAACGGGAAAGAATATAACAGTTGCACAGACACCGGTCGCTCAGATGGTTTTTTATG

GTGCTCAACAACGTATAACTTCGAAAAGGATGGGAAGTACGGATTTTGTCCGGATCAGG

GTTATAGCCTG

DNA sequence encoding exemplary peptide 111 (with stop codon)

SEQ ID NO: 24

GAAGGTCAGGTTGTTCGTGTGAAATATGTTAATGCCGATGGCGAGTATTGCAAATTTCC

GTTTCTGTTTAACGGCAAAGAGTATAATAGCTGTACCGATACCGGTCGTAGTGATGGTT

TTCTGTGGTGTAGCACCACCTATAACTTTGAGAAAGATGGCAAATATGGCTTTTGTCCG

CATGAAGCACTGTTTGTGATGTATGTGAATGCGGATGGTGAATACTGTAAATTCCCCTTT

CTGTTCAATGGTAAAGAATACAACTCATGCACCGATACAGGCCGTTCAGATGGCTTTCG

TTGGTGTTCAACCACCTACAATTTCGAAAAAGACGGTAAGTATGGTTTCTGTCCGGAAA

CCGCAGTGCGCGTTAAATATGTGAACGCAGATGGGGAATATTGTAAGTTTCCGTTCTTA

TTCAACGGGAAAGAATATAACAGTTGCACAGACACCGGTCGCTCAGATGGTTTTTTATG

GTGCTCAACAACGTATAACTTCGAAAAGGATGGGAAGTACGGATTTTGTCCGGATCAGG

GTTATAGCCTGTAA

Exemplary peptide 222 comprising three modules corresponding to module 2 of the CBD of
MMP-2

SEQ ID NO: 25

EGQVVFTMYGNAEGQPCKFPFRFQGTSYDSCTTEGRTDGYRWCGTTEDYDRDKKYGFC

PHEALFTMGGNAEGQPCKFPFRFQGTSYDSCTTEGRTDGYRWCGTTEDYDRDKKYGFCP

ETALFTMGGNAEGQPCKFPFRFQGTSYDSCTTEGRTDGYRWCGTTEDYDRDKKYGFCPD

QGYSL

DNA sequence encoding exemplary peptide 222

SEQ ID NO: 26

GAAGGTCAGGTTGTGTTTACCATGTATGGTAATGCCGAAGGTCAGCCGTGTAAATTTCCGTTTCGTTT

TCAGGGCACCAGCTATGATAGTTGTACCACCGAAGGTCGTACCGATGGTTATCGTTGGTGTGGTACGA

CCGAAGATTATGATCGTGATAAAAAGTATGGCTTTTGTCCGCATGAAGCCCTGTTTACAATGGGTGGC

AATGCAGAGGGCCAGCCTTGCAAATTCCCTTTTCGCTTCCAGGGTACATCTTATGATTCATGCACAAC

```
GGAAGGTCGCACAGATGGCTACCGCTGGTGCGGCACCACAGAGGATTATGACCGCGACAAAAAATACG

GTTTTTGTCCGGAAACCGCACTGTTCACCATGGGTGGTAATGCGGAAGGACAACCATGCAAGTTTCCA

TTCCGCTTTCAGGGAACCTCATATGATAGCTGCACAACAGAGGGACGTACGGATGGATACAGATGGTG

CGGTACAACCGAGGACTACGATAGAGATAAGAAATATGGTTTCTGTCCCGATCAGGGTTATAGCCTG
```

Exemplary peptide 333 comprising three modules corresponding to module 3 of the CBD of MMP-2

SEQ ID NO: 27

E G Q V V S T V Y G N S E G A P C V F P F T F L G N K Y E S C T S A G R S D G F L W C
A T T A N Y D D D R K W G F C P H E A L F T M G G N S E G A P C V F P F T F L G N K Y
E S C T S A G R S D G K R W C A T T A N Y D D D R K W G F C P E T A M S T V G G N S
E G A P C V F P F T F L G N K Y E S C T S A G R S D G K M W C A T T A N Y D D D R K
W G F C P D Q G Y S L

DNA encoding exemplary peptide 333

SEQ ID NO: 28

```
GAAGGTCAGGTTGTTAGCACCGTTTATGGTAATAGCGAAGGTGCACCGTGTGTTTTTCC

GTTTACCTTTCTGGGTAACAAATATGAAAGCTGTACCAGCGCAGGTCGTAGTGATGGTT

TTCTGTGGTGTGCAACCACCGCAAATTATGATGATGATCGTAAATGGGGTTTTTGTCCG

CATGAAGCACTGTTTACCATGGGTGGCAATTCTGAAGGTGCCCCTTGCGTGTTTCCTTT

TACATTTTTAGGCAACAAGTACGAAAGCTGCACCTCAGCCGGTCGTTCAGATGGTAAAC

GTTGGTGCGCCACCACAGCCAACTATGATGACGACAGAAATGGGGCTTCTGTCCTGA

AACCGCAATGAGCACCGTTGGTGGCAACAGTGAAGGCGCTCCATGCGTTTTCCCGTTC

ACATTCCTGGGCAATAAATACGAATCATGTACCTCTGCAGGTCGCTCTGATGGCAAAAT

GTGGTGCGCGACAACGGCCAATTACGACGATGACCGCAAGTGGGGCTTTTGCCCAGAT

CAGGGTTATAGCCTG
```

Linker sequence 1

SEQ ID NO: 29

EGQV

Amino acid sequence comprising a peptide comprising module 3 of CBD of MMP-9. The residues that are not underlined constitute module 3. The underlined residues may optionally be added to assist expression of the sequence.

SEQ ID NO: 30

<u>STVMGG</u>NSAGELCVFPFTFLGKEYSTCTSEGRGDGRLWCATTSNFDSDKKWGFC
PD<u>QG</u>

Amino acid sequence comprising CBD of MMP-9. The residues that are not underlined constitute the CBD. The underlined residues may optionally be added to assist expression of the sequence

SEQ ID NO: 31

<u>PTRFGN</u>ADGAACHFPFIFEGRSYSACTTDGRSDGLPWCSTTANYDTDDRFGFCPS

ERLYTQDGNADGKPCQFPFIFQGQSYSACTTDGRSDGYRWCATTANYDRDKLFG

FCPTRADSTVMGGNSAGELCVFPFTFLGKEYSTCTSEGRGDGRLWCATTSNFDS

DKKWGFCPD<u>QGYS</u>

Linker sequence 4

SEQ ID NO: 32

DQGYSL

Amino acid sequence of full length MMP-9

SEQ ID NO: 33

MSLWQPLVLV LLVLGCCFAA PRQRSTLVL FPGDLRTNLT DRQLAEEYLY RYGYTRVAEM

RGESKSLGPA LLLLQKQLSL PETGELDSAT LKAMRTPRCG VPDLGRFQTF EGDLKWHHHN

ITYWIQNYSE DLPRAVIDDA FARAFALWSA VTPLTFTRVY SRDADIVIQF GVAEHGDGYP

FDGKDGLLAH AFPPGPGIQG DAHFDDDELW SLGKGVVVPT RFGNADGAAC HFPFIFEGRS

```
YSACTTDGRS DGLPWCSTTA NYDTDDRFGF CPSERLYTQD GNADGKPCQF PFIFQGQSYS

ACTTDGRSDG YRWCATTANY DRDKLFGFCP TRADSTVMGG NSAGELCVFP FTFLGKEYST

CTSEGRGDGR LWCATTSNFD SDKKWGFCPD QGYSLFLVAA HEFGHALGLD HSSVPEALMY

PMYRFTEGPP LHKDDVNGIR HLYGPRPEPE PRPPTTTTPQ PTAPPTVCPT GPPTVHPSER

PTAGPTGPPS AGPTGPPTAG PSTATTVPLS PVDDACNVNI FDAIAEIGNQ LYLFKDGKYW

RFSEGRGSRP QGPFLIADKW PALPRKLDSV FEERLSKKLF FFSGRQVWVY TGASVLGPRR

LDKLGLGADV AQVTGALRSG RGKMLLFSGR RLWRFDVKAQ MVDPRSASEV DRMFPGVPLD

THDVFQYREK AYFCQDRFYW RVSSRSELNQ VDQVGYVTYD ILQCPED

Amino acid sequence of module 1 of CBD of MMP-9
                                                              SEQ ID NO: 34
ADGAACHFPFIFEGRSYSACTTDGRSDGLPWCSTTANYDTDDRFGFCPS Amino acid sequence of a peptide comprising module 1 of CBD of MMP-9. The residues that
are not underlined constitute module 1. The underlined residues may optionally be added to
assist expression of the sequence.
                                                              SEQ ID NO: 35
TRFGNADGAACHFPFIFEGRSYSACTTDGRSDGLPWCSTTANYDTDDRFGFCPSE

RLYTQ

Amino acid sequence of Module 2 of CBD of MMP-9
                                                              SEQ ID NO: 36
ADGKPCQFPFIFQGQSYSACTTDGRSDGYRWCATTANYDRDKLFGFCPT Amino acid sequence of a peptide comprising module 2 of CBD of MMP-9. The residues that
are not underlined constitute module 2. The underlined residues may optionally be added to
assist expression of the sequence.
                                                              SEQ ID NO: 37
RLYTQDGNADGKPCQFPFIFQGQSYSACTTDGRSDGYRWCATTANYDRDKLFGF

CPTRA

Amino acid sequence of Module 3 of CBD of MMP-9
                                                              SEQ ID NO: 38
SAGELCVFPFTFLGKEYSTCTSEGRGDGRLWCATTSNFDSDKKWGFCPD
```

TABLE 1

Binding affinity of individual modules of CBD of MMP-2 and peptides comprising three modules corresponding to module 2 (222) and three modules corresponding to module 3 (333) to collagen type II and type I gelatin. Measured by ELISA binding assay (Kd (nM)).

|  | Kd on Type II gelatin (nM) | Kd on Type I gelatin (nM) |
|---|---|---|
| Full length CBD | 20.4 ± 2.31 (n = 3) | 2.58 (n = 1) |
| Module 1 | 1,660 ± 160 (n = 2) | 4,770 ± 1,880 (n = 2) |
| Module 2 | 4,260 ± 253 (n = 2) | 3,720 |
| Module 3 | 12,000 ± 494 (n = 2) | 4,090 |
| 222 | 1.46 ± 0.53 (n = 4) | 0.497 (n = 1) |
| 333 | 117 ± 18.9 (n = 3) | 0.0159 (n = 1) |

TABLE 2

Summary of all binding data, all ratios are protein:ligand

|  | Gelatin sepharose (bovine skin Type I collagen gelatin) | | NMR - Type II collagen | NMR - Type I collagen peptide | |
|---|---|---|---|---|---|
|  | Experimental data | Previously published data | gelatin Experimental data | Experimental data | Previously published data |
| Wild Type CBD | Good Binding |  | Binding at a 40:1 ratio. Modules affinity: M2 > M1 > M3 | N/A |  |

TABLE 2-continued

Summary of all binding data, all ratios are protein:ligand

| | Gelatin sepharose (bovine skin Type I collagen gelatin) | | NMR - Type II collagen | | NMR - Type I collagen peptide | |
|---|---|---|---|---|---|---|
| | Experimental data | Previously published data | gelatin Experimental data | Experimental data | Previously published data | |
| Module 1 (M1) | No binding | Modules affinity: M2 > M3 >> M1 | Binding at a 2:1 ratio | Binding at a 1:5 ratio | All modules bind. Affinity: M2 > M3 >> M1 | |
| Module 2 (M2) | Good Binding | | N/A | N/A | | |
| Module 3 (M3) | Good Binding | | N/A | Binding at a 1:5 ratio | | |

TABLE 3

NMR analysis showed which residues of modules 1 and 2 of the CBD of MMP-2 were important for binding to collagen type II gelatin

| Module | Residues shown to be important in binding (NMR) |
|---|---|
| Module 2 within FL CBD (MMP-2) | G299, G313, G309, T319, Y314, W316, F297, Y302, Y325 |
| Module 1 | G241, G251, N264, T261, E266, Y244, L238, N240, F265, K267, R252, D268, F239 |

TABLE 4

Dynamic Light scattering was used to measure both the hydrodynamic radius and the zeta potential of a peptide, confirming that the two-step conjugation process was successful

| | Zeta potential (mV) | Size (nm) |
|---|---|---|
| Native FITC-222 | −18.6 | 3.32 |
| Cationised FITC - 222 | 17.8 | 3.815 |
| Surfactant FITC - 222 | −0.89 | 7.65 |

TABLE 5

Predicting CBD residues involved in binding to Type II collagen based on published Type I collagen peptide data

| | Type I collagen peptide | | | |
|---|---|---|---|---|
| Module | Residues involved in binding | Most ligand-sensitive residues | Kd (M) | Gelatin sepharose Ka (mM$^{-1}$) |
| Module 1 | K224, N227, K234, N240, G241, Y244, D249, R252, W258, T262, N264, E266 | R252 > E266 > T262 | 6.0 10-4 | 0.4 |
| Module 2 | Q289, R296, F297, G299, Y302, C305, G309, R310, Y314, C317, E321, Y323, Y329, and G330 | G309 > Y323 > F297 > G299 > Y329 | 2.8 10-4 | 1.6 |
| Module 3 | G357, Y360, C363, A366, R368, W374, C375, T377, Y381, and K386 | R368 > Y381 > W374 | 3.4.10-4 | 1.3 |

```
                     SEQUENCE LISTING

<160> NUMBER OF SEQ ID NOS: 38

<210> SEQ ID NO 1
<211> LENGTH: 660
<212> TYPE: PRT
<213> ORGANISM: Homo sapiens

<400> SEQUENCE: 1

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
                20                  25                  30

Pro Ile Ile Lys Phe Pro Gly Asp Val Ala Pro Lys Thr Asp Lys Glu
            35                  40                  45

Leu Ala Val Gln Tyr Leu Asn Thr Phe Tyr Gly Cys Pro Lys Glu Ser
        50                  55                  60
```

```
Cys Asn Leu Phe Val Leu Lys Asp Thr Leu Lys Met Gln Lys Phe
 65                  70                  75                  80

Phe Gly Leu Pro Gln Thr Gly Asp Leu Asp Gln Asn Thr Ile Glu Thr
                 85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
            115                 120                 125

Ile Gly Tyr Thr Pro Asp Leu Asp Pro Glu Thr Val Asp Asp Ala Phe
    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
            195                 200                 205

Asp Asp Glu Leu Trp Thr Leu Gly Glu Gly Gln Val Val Arg Val Lys
210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
            275                 280                 285

Gln Pro Cys Lys Phe Pro Phe Arg Phe Gln Gly Thr Ser Tyr Asp Ser
            290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
            355                 360                 365

Ser Asp Gly Lys Met Trp Cys Ala Thr Thr Ala Asn Tyr Asp Asp Asp
            370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
            420                 425                 430

Leu Ser Gln Asp Asp Ile Lys Gly Ile Gln Glu Leu Tyr Gly Ala Ser
            435                 440                 445

Pro Asp Ile Asp Leu Gly Thr Gly Pro Thr Pro Thr Leu Gly Pro Val
            450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
```

```
                        485                 490                 495
Val Thr Pro Arg Asp Lys Pro Met Gly Pro Leu Leu Val Ala Thr Phe
                500                 505                 510

Trp Pro Glu Leu Pro Glu Lys Ile Asp Ala Val Tyr Glu Ala Pro Gln
            515                 520                 525

Glu Glu Lys Ala Val Phe Phe Ala Gly Asn Glu Tyr Trp Ile Tyr Ser
        530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
                580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
        610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 2
<211> LENGTH: 165
<212> TYPE: PRT
<213> ORGANISM: Homo sapiens

<400> SEQUENCE: 2

Ala Asp Gly Glu Tyr Cys Lys Phe Pro Phe Leu Phe Asn Gly Lys Glu
1               5                   10                  15

Tyr Asn Ser Cys Thr Asp Thr Gly Arg Ser Asp Gly Phe Leu Trp Cys
            20                  25                  30

Ser Thr Thr Tyr Asn Phe Glu Lys Asp Gly Lys Tyr Gly Phe Cys Pro
        35                  40                  45

His Glu Ala Leu Phe Thr Met Gly Gly Asn Ala Glu Gly Gln Pro Cys
50                  55                  60

Lys Phe Pro Phe Arg Phe Gln Gly Thr Ser Tyr Asp Ser Cys Thr Thr
65                  70                  75                  80

Glu Gly Arg Thr Asp Gly Tyr Arg Trp Cys Gly Thr Thr Glu Asp Tyr
            85                  90                  95

Asp Arg Asp Lys Lys Tyr Gly Phe Cys Pro Glu Thr Ala Met Ser Thr
        100                 105                 110

Val Gly Gly Asn Ser Glu Gly Ala Pro Cys Val Phe Pro Phe Thr Phe
    115                 120                 125

Leu Gly Asn Lys Tyr Glu Ser Cys Thr Ser Ala Gly Arg Ser Asp Gly
130                 135                 140

Lys Met Trp Cys Ala Thr Thr Ala Asn Tyr Asp Asp Asp Arg Lys Trp
145                 150                 155                 160

Gly Phe Cys Pro Asp
            165

<210> SEQ ID NO 3
<211> LENGTH: 175
```

<212> TYPE: PRT
<213> ORGANISM: Artificial Sequence
<220> FEATURE:
<223> OTHER INFORMATION: Amino acid sequence of peptide comprising the
      CBD of MMP-2 with additional residues added

<400> SEQUENCE: 3

Arg Val Lys Tyr Gly Asn Ala Asp Gly Glu Tyr Cys Lys Phe Pro Phe
1               5                   10                  15

Leu Phe Asn Gly Lys Glu Tyr Asn Ser Cys Thr Asp Thr Gly Arg Ser
            20                  25                  30

Asp Gly Phe Leu Trp Cys Ser Thr Thr Tyr Asn Phe Glu Lys Asp Gly
        35                  40                  45

Lys Tyr Gly Phe Cys Pro His Glu Ala Leu Phe Thr Met Gly Gly Asn
    50                  55                  60

Ala Glu Gly Gln Pro Cys Lys Phe Pro Phe Arg Phe Gln Gly Thr Ser
65                  70                  75                  80

Tyr Asp Ser Cys Thr Thr Glu Gly Arg Thr Asp Gly Tyr Arg Trp Cys
                85                  90                  95

Gly Thr Thr Glu Asp Tyr Asp Arg Asp Lys Lys Tyr Gly Phe Cys Pro
            100                 105                 110

Glu Thr Ala Met Ser Thr Val Gly Gly Asn Ser Glu Gly Ala Pro Cys
        115                 120                 125

Val Phe Pro Phe Thr Phe Leu Gly Asn Lys Tyr Glu Ser Cys Thr Ser
    130                 135                 140

Ala Gly Arg Ser Asp Gly Lys Met Trp Cys Ala Thr Thr Ala Asn Tyr
145                 150                 155                 160

Asp Asp Asp Arg Lys Trp Gly Phe Cys Pro Asp Gln Gly Tyr Ser
                165                 170                 175

<210> SEQ ID NO 4
<211> LENGTH: 525
<212> TYPE: DNA
<213> ORGANISM: Homo sapiens

<400> SEQUENCE: 4
cgtgtgaaat atggtaatgc cgatggcgaa tattgcaaat tccgtttct gtttaacggc      60 aaagagtata atagctgtac cgataccggt cgtagtgatg gttttctgtg gtgtagcacc     120
acctataact ttgagaaaga tggcaaatat ggcttttgtc cgcatgaagc actgtttacc     180
atgggtggta atgcggaagg tcagccgtgt aaatttcctt ttcgctttca gggcaccagc     240
tatgatagtt gtaccaccga aggtcgtacc gatggttatc gttggtgcgg tacaaccgaa     300
gattatgatc gtgacaaaaa atacggttc tgtccggaaa ccgcaatgag caccgttggt      360
ggtaatagtg aaggtgcacc gtgtgttttt ccgtttacct ttctgggtaa caaatatgaa     420
agctgtacca gtgcaggtcg ttcagatggt aaaatgtggt gcgcaaccac cgcaaattat     480
gatgatgatc gtaaatgggg tttttgccca gatcagggtt atagc                    525

<210> SEQ ID NO 5
<211> LENGTH: 528
<212> TYPE: DNA
<213> ORGANISM: Artificial Sequence
<220> FEATURE:
<223> OTHER INFORMATION: DNA sequence encoding the CBD of MMP-2 (with
      stop codon)

<400> SEQUENCE: 5
cgtgtgaaat atggtaatgc cgatggcgaa tattgcaaat tccgtttct gtttaacggc      60

-continued

```
aaagagtata atagctgtac cgataccggt cgtagtgatg gttttctgtg gtgtagcacc    120
acctataact ttgagaaaga tggcaaatat ggcttttgtc cgcatgaagc actgtttacc    180
atgggtggta atgcggaagg tcagccgtgt aaatttcctt ttcgctttca gggcaccagc    240
tatgatagtt gtaccaccga aggtcgtacc gatggttatc gttggtgcgg tacaaccgaa    300
gattatgatc gtgacaaaaa atacggtttc tgtccggaaa ccgcaatgag caccgttggt    360
ggtaatagtg aaggtgcacc gtgtgttttt ccgtttacct ttctgggtaa caaatatgaa    420
agctgtacca gtgcaggtcg ttcagatggt aaaatgtggt gcgcaaccac cgcaaattat    480
gatgatgatc gtaaatgggg ttttttgccca gatcagggtt atagctaa                528
```

<210> SEQ ID NO 6
<211> LENGTH: 49
<212> TYPE: PRT
<213> ORGANISM: Homo sapiens

<400> SEQUENCE: 6

Ala Asp Gly Glu Tyr Cys Lys Phe Pro Phe Leu Phe Asn Gly Lys Glu
1               5                   10                  15

Tyr Asn Ser Cys Thr Asp Thr Gly Arg Ser Asp Gly Phe Leu Trp Cys
            20                  25                  30

Ser Thr Thr Tyr Asn Phe Glu Lys Asp Gly Lys Tyr Gly Phe Cys Pro
        35                  40                  45

His

<210> SEQ ID NO 7
<211> LENGTH: 60
<212> TYPE: PRT
<213> ORGANISM: Artificial Sequence
<220> FEATURE:
<223> OTHER INFORMATION: Amino acid sequence comprising module 1 of the
      CBD of MMP-2 with additional residues

<400> SEQUENCE: 7

Val Lys Tyr Gly Asn Ala Asp Gly Glu Tyr Cys Lys Phe Pro Phe Leu
1               5                   10                  15

Phe Asn Gly Lys Glu Tyr Asn Ser Cys Thr Asp Thr Gly Arg Ser Asp
            20                  25                  30

Gly Phe Leu Trp Cys Ser Thr Thr Tyr Asn Phe Glu Lys Asp Gly Lys
        35                  40                  45

Tyr Gly Phe Cys Pro His Glu Ala Leu Phe Thr Met
    50                  55                  60

<210> SEQ ID NO 8
<211> LENGTH: 55
<212> TYPE: PRT
<213> ORGANISM: Artificial Sequence
<220> FEATURE:
<223> OTHER INFORMATION: a variant module corresponding to module 1 of
      the CBD of MMP-2

<400> SEQUENCE: 8

Val Arg Val Lys Tyr Val Asn Ala Asp Gly Glu Tyr Cys Lys Phe Pro
1               5                   10                  15

Phe Leu Phe Asn Gly Lys Glu Tyr Asn Ser Cys Thr Asp Thr Gly Arg
            20                  25                  30

Ser Asp Gly Phe Leu Trp Cys Ser Thr Thr Tyr Asn Phe Glu Lys Asp
        35                  40                  45

Gly Lys Tyr Gly Phe Cys Pro
    50              55

<210> SEQ ID NO 9
<211> LENGTH: 180
<212> TYPE: DNA
<213> ORGANISM: Homo sapiens

<400> SEQUENCE: 9
gtgaaatatg gtaatgccga tgcgaatat tgcaaatttc cgtttctgtt taacggcaaa     60
gagtataata gctgtaccga taccggtcgt agtgatggtt ttctgtggtg tagcaccacc   120
tataactttg agaaagatgg caaatatggc ttttgtccgc atgaagcact gtttaccatg   180

<210> SEQ ID NO 10
<211> LENGTH: 183
<212> TYPE: DNA
<213> ORGANISM: Artificial Sequence
<220> FEATURE:
<223> OTHER INFORMATION: DNA sequence encoding an amino acid sequence
      comprising module 1 of the CBD of MMP-2 with stop codon

<400> SEQUENCE: 10
gtgaaatatg gtaatgccga tgcgaatat tgcaaatttc cgtttctgtt taacggcaaa     60
gagtataata gctgtaccga taccggtcgt agtgatggtt ttctgtggtg tagcaccacc   120
tataactttg agaaagatgg caaatatggc ttttgtccgc atgaagcact gtttaccatg   180
taa                                                                 183

<210> SEQ ID NO 11
<211> LENGTH: 49
<212> TYPE: PRT
<213> ORGANISM: Homo sapiens

<400> SEQUENCE: 11

Ala Glu Gly Gln Pro Cys Lys Phe Pro Phe Arg Phe Gln Gly Thr Ser
1               5                   10                  15

Tyr Asp Ser Cys Thr Thr Glu Gly Arg Thr Asp Gly Tyr Arg Trp Cys
            20                  25                  30

Gly Thr Thr Glu Asp Tyr Asp Arg Asp Lys Lys Tyr Gly Phe Cys Pro
        35                  40                  45

Glu

<210> SEQ ID NO 12
<211> LENGTH: 59
<212> TYPE: PRT
<213> ORGANISM: Artificial Sequence
<220> FEATURE:
<223> OTHER INFORMATION: Amino acid sequence comprising module 2 of the
      CBD of MMP-2 with additional residues

<400> SEQUENCE: 12

Ala Leu Phe Thr Met Gly Gly Asn Ala Glu Gly Gln Pro Cys Lys Phe
1               5                   10                  15

Pro Phe Arg Phe Gln Gly Thr Ser Tyr Asp Ser Cys Thr Thr Glu Gly
            20                  25                  30

Arg Thr Asp Gly Tyr Arg Trp Cys Gly Thr Thr Glu Asp Tyr Asp Arg
        35                  40                  45

Asp Lys Lys Tyr Gly Phe Cys Pro Glu Thr Ala
    50                  55

```
<210> SEQ ID NO 13
<211> LENGTH: 55
<212> TYPE: PRT
<213> ORGANISM: Homo sapiens

<400> SEQUENCE: 13

Val Phe Thr Met Tyr Gly Asn Ala Glu Gly Gln Pro Cys Lys Phe Pro
1               5                   10                  15

Phe Arg Phe Gln Gly Thr Ser Tyr Asp Ser Cys Thr Thr Glu Gly Arg
            20                  25                  30

Thr Asp Gly Tyr Arg Trp Cys Gly Thr Thr Glu Asp Tyr Asp Arg Asp
        35                  40                  45

Lys Lys Tyr Gly Phe Cys Pro
    50                  55

<210> SEQ ID NO 14
<211> LENGTH: 55
<212> TYPE: PRT
<213> ORGANISM: Artificial Sequence
<220> FEATURE:
<223> OTHER INFORMATION: Amino acid sequence of a variant module
      corresponding to module 2 of the CBD of MMP-2

<400> SEQUENCE: 14

Leu Phe Thr Met Gly Gly Asn Ala Glu Gly Gln Pro Cys Lys Phe Pro
1               5                   10                  15

Phe Arg Phe Gln Gly Thr Ser Tyr Asp Ser Cys Thr Thr Glu Gly Arg
            20                  25                  30

Thr Asp Gly Tyr Arg Trp Cys Gly Thr Thr Glu Asp Tyr Asp Arg Asp
        35                  40                  45

Lys Lys Tyr Gly Phe Cys Pro
    50                  55

<210> SEQ ID NO 15
<211> LENGTH: 177
<212> TYPE: DNA
<213> ORGANISM: Artificial Sequence
<220> FEATURE:
<223> OTHER INFORMATION: DNA sequence encoding a peptide comprising a
      variant module corresponding to module 2 of the CBD of MMP-2

<400> SEQUENCE: 15
gcactgttta ccatgggtgg taatgcggaa ggtcagccgt gtaaatttcc ttttcgcttt      60
cagggcacca gctatgatag ttgtaccacc gaaggtcgta ccgatggtta cgttggtgc     120 ggtacaaccg aagattatga tcgtgacaaa aaatacggtt tctgtccgga aaccgca       177

<210> SEQ ID NO 16
<211> LENGTH: 180
<212> TYPE: DNA
<213> ORGANISM: Artificial Sequence
<220> FEATURE:
<223> OTHER INFORMATION: DNA sequence encoding a peptide comprising a
      module corresponding to module 2 of the CBD of MMP-2 with stop
      codon

<400> SEQUENCE: 16
gcactgttta ccatgggtgg taatgcggaa ggtcagccgt gtaaatttcc ttttcgcttt      60
cagggcacca gctatgatag ttgtaccacc gaaggtcgta ccgatggtta cgttggtgc     120 ggtacaaccg aagattatga tcgtgacaaa aaatacggtt tctgtccgga aaccgcataa   180

<210> SEQ ID NO 17
```

```
<211> LENGTH: 49
<212> TYPE: PRT
<213> ORGANISM: Homo sapiens

<400> SEQUENCE: 17

Ser Glu Gly Ala Pro Cys Val Phe Pro Phe Thr Phe Leu Gly Asn Lys
1               5                   10                  15

Tyr Glu Ser Cys Thr Ser Ala Gly Arg Ser Asp Gly Lys Met Trp Cys
            20                  25                  30

Ala Thr Thr Ala Asn Tyr Asp Asp Arg Lys Trp Gly Phe Cys Pro
        35                  40                  45

Asp

<210> SEQ ID NO 18
<211> LENGTH: 58
<212> TYPE: PRT
<213> ORGANISM: Artificial Sequence
<220> FEATURE:
<223> OTHER INFORMATION: Amino acid sequence of a peptide comprising
      module 3 of the CBD of MMP-2 with additional residues

<400> SEQUENCE: 18

Met Ser Thr Val Gly Gly Asn Ser Glu Gly Ala Pro Cys Val Phe Pro
1               5                   10                  15

Phe Thr Phe Leu Gly Asn Lys Tyr Glu Ser Cys Thr Ser Ala Gly Arg
            20                  25                  30

Ser Asp Gly Lys Met Trp Cys Ala Thr Thr Ala Asn Tyr Asp Asp Asp
        35                  40                  45

Arg Lys Trp Gly Phe Cys Pro Asp Gln Gly
    50                  55

<210> SEQ ID NO 19
<211> LENGTH: 55
<212> TYPE: PRT
<213> ORGANISM: Artificial Sequence
<220> FEATURE:
<223> OTHER INFORMATION: Amino acid sequence of a variant module
      corresponding to module 3 of the CBD of MMP-2

<400> SEQUENCE: 19

Met Ser Thr Val Gly Gly Asn Ser Glu Gly Ala Pro Cys Val Phe Pro
1               5                   10                  15

Phe Thr Phe Leu Gly Asn Lys Tyr Glu Ser Cys Thr Ser Ala Gly Arg
            20                  25                  30

Ser Asp Gly Lys Met Trp Cys Ala Thr Thr Ala Asn Tyr Asp Asp Asp
        35                  40                  45

Arg Lys Trp Gly Phe Cys Pro
    50                  55

<210> SEQ ID NO 20
<211> LENGTH: 174
<212> TYPE: DNA
<213> ORGANISM: Homo sapiens

<400> SEQUENCE: 20
atgagcaccg ttggtggtaa tagtgaaggt gcaccgtgtg ttttccgtt tacctttctg      60 ggtaacaaat atgaaagctg taccagtgca ggtcgttcag atggtaaaat gtggtgcgca     120
accaccgcaa attatgatga tgatcgtaaa tggggttttt gcccagatca gggt           174

<210> SEQ ID NO 21
```

<211> LENGTH: 177
<212> TYPE: DNA
<213> ORGANISM: Artificial Sequence
<220> FEATURE:
<223> OTHER INFORMATION: DNA encoding a peptide comprising a module
      corresponding to module 3 of the CBD of MMP-2 with stop codon

<400> SEQUENCE: 21
atgagcaccg ttggtggtaa tagtgaaggt gcaccgtgtg tttttccgtt taccttctg     60 ggtaacaaat atgaaagctg taccagtgca ggtcgttcag atggtaaaat gtggtgcgca   120
accaccgcaa attatgatga tgatcgtaaa tggggttttt gcccagatca gggttaa     177

<210> SEQ ID NO 22
<211> LENGTH: 181
<212> TYPE: PRT
<213> ORGANISM: Artificial Sequence
<220> FEATURE:
<223> OTHER INFORMATION: Exemplary peptide 111 comprising three modules
      corresponding to module 1 of the CBD of MMP-2

<400> SEQUENCE: 22

Glu Gly Gln Val Val Arg Val Lys Tyr Gly Asn Ala Asp Gly Glu Tyr
1               5                   10                  15

Cys Lys Phe Pro Phe Leu Phe Asn Gly Lys Glu Tyr Asn Ser Cys Thr
                20                  25                  30

Asp Thr Gly Arg Ser Asp Gly Phe Leu Trp Cys Ser Thr Thr Tyr Asn
            35                  40                  45

Phe Glu Lys Asp Gly Lys Tyr Gly Phe Cys Pro His Glu Ala Leu Phe
        50                  55                  60

Val Met Tyr Gly Asn Ala Asp Gly Glu Tyr Cys Lys Phe Pro Phe Leu
65                  70                  75                  80

Phe Asn Gly Lys Glu Tyr Asn Ser Cys Thr Asp Thr Gly Arg Ser Asp
                85                  90                  95

Gly Phe Arg Trp Cys Ser Thr Thr Tyr Asn Phe Glu Lys Asp Gly Lys
            100                 105                 110

Tyr Gly Phe Cys Pro Glu Thr Ala Val Arg Val Lys Tyr Gly Asn Ala
        115                 120                 125

Asp Gly Glu Tyr Cys Lys Phe Pro Phe Leu Phe Asn Gly Lys Glu Tyr
    130                 135                 140

Asn Ser Cys Thr Asp Thr Gly Arg Ser Asp Gly Phe Leu Trp Cys Ser
145                 150                 155                 160

Thr Thr Tyr Asn Phe Glu Lys Asp Gly Lys Tyr Gly Phe Cys Pro Asp
                165                 170                 175

Gln Gly Tyr Ser Leu
            180

<210> SEQ ID NO 23
<211> LENGTH: 543
<212> TYPE: DNA
<213> ORGANISM: Artificial Sequence
<220> FEATURE:
<223> OTHER INFORMATION: DNA sequence encoding exemplary peptide 111

<400> SEQUENCE: 23
gaaggtcagg ttgttcgtgt gaaatatggt aatgcagatg gcgagtattg caaatttccg     60 tttctgtttta acggcaaaga gtataatagc tgtaccgata ccggtcgtag tgatggtttt   120
ctgtggtgta gcaccaccta taactttgag aaagatggca aatatggctt tgtccgcat    180 gaagcactgt ttgtgatgta tggcaatgcc gatggtgaat actgtaaatt cccatttctg   240

```
ttcaatggta aagaatacaa ctcatgcacc gatacaggcc gttcagatgg ctttcgttgg    300
tgttcaacca cctacaattt cgaaaaagac ggtaagtatg gtttctgtcc ggaaaccgca    360
gtgcgcgtta aatatggcaa cgcggacggg gaatattgta agtttccgtt cttattcaac    420
gggaaagaat ataacagttg cacagacacc ggtcgctcag atggttttt atggtgctca    480 acaacgtata acttcgaaaa ggatgggaag tacggatttt gtccggatca gggttatagc    540
ctg                                                                  543

<210> SEQ ID NO 24
<211> LENGTH: 546
<212> TYPE: DNA
<213> ORGANISM: Artificial Sequence
<220> FEATURE:
<223> OTHER INFORMATION: DNA sequence encoding exemplary peptide 111
      (with stop codon)

<400> SEQUENCE: 24
gaaggtcagg ttgttcgtgt gaaatatgtt aatgccgatg gcgagtattg caaatttccg     60
tttctgttta acggcaaaga gtataatagc tgtaccgata ccggtcgtag tgatggtttt    120
ctgtggtgta gcaccaccta aactttgag aaagatggca aatatggctt ttgtccgcat    180
gaagcactgt ttgtgatgta tgtgaatgcg gatggtgaat actgtaaatt ccccttttctg   240 ttcaatggta aagaatacaa ctcatgcacc gatacaggcc gttcagatgg ctttcgttgg    300
tgttcaacca cctacaattt cgaaaaagac ggtaagtatg gtttctgtcc ggaaaccgca    360
gtgcgcgtta aatatgtgaa cgcagacggg gaatattgta agtttccgtt cttattcaac    420
gggaaagaat ataacagttg cacagacacc ggtcgctcag atggttttt atggtgctca    480 acaacgtata acttcgaaaa ggatgggaag tacggatttt gtccggatca gggttatagc    540
ctgtaa                                                               546

<210> SEQ ID NO 25
<211> LENGTH: 181
<212> TYPE: PRT
<213> ORGANISM: Artificial Sequence
<220> FEATURE:
<223> OTHER INFORMATION: Exemplary peptide 222 comprising three modules
      corresponding to module 2 of the CBD of MMP-2

<400> SEQUENCE: 25

Glu Gly Gln Val Val Phe Thr Met Tyr Gly Asn Ala Glu Gly Gln Pro
1               5                   10                  15

Cys Lys Phe Pro Phe Arg Phe Gln Gly Thr Ser Tyr Asp Ser Cys Thr
            20                  25                  30

Thr Glu Gly Arg Thr Asp Gly Tyr Arg Trp Cys Gly Thr Thr Glu Asp
        35                  40                  45

Tyr Asp Arg Asp Lys Lys Tyr Gly Phe Cys Pro His Glu Ala Leu Phe
    50                  55                  60

Thr Met Gly Gly Asn Ala Glu Gly Gln Pro Cys Lys Phe Pro Phe Arg
65                  70                  75                  80

Phe Gln Gly Thr Ser Tyr Asp Ser Cys Thr Thr Glu Gly Arg Thr Asp
                85                  90                  95

Gly Tyr Arg Trp Cys Gly Thr Thr Glu Asp Tyr Asp Arg Asp Lys Lys
            100                 105                 110

Tyr Gly Phe Cys Pro Glu Thr Ala Leu Phe Thr Met Gly Gly Asn Ala
        115                 120                 125
```

```
Glu Gly Gln Pro Cys Lys Phe Pro Phe Arg Phe Gln Gly Thr Ser Tyr
        130                 135                 140
Asp Ser Cys Thr Thr Glu Gly Arg Thr Asp Gly Tyr Arg Trp Cys Gly
145                 150                 155                 160
Thr Thr Glu Asp Tyr Asp Arg Asp Lys Lys Tyr Gly Phe Cys Pro Asp
                165                 170                 175
Gln Gly Tyr Ser Leu
            180

<210> SEQ ID NO 26
<211> LENGTH: 543
<212> TYPE: DNA
<213> ORGANISM: Artificial Sequence
<220> FEATURE:
<223> OTHER INFORMATION: DNA sequence encoding exemplary peptide 222

<400> SEQUENCE: 26
gaaggtcagg ttgtgtttac catgtatggt aatgccgaag gtcagccgtg taaatttccg      60
tttcgttttc agggcaccag ctatgatagt tgtaccaccg aaggtcgtac cgatggttat     120
cgttggtgtg gtacgaccga agattatgat cgtgataaaa agtatggctt tgtccgcat     180 gaagccctgt ttacaatggg tggcaatgca gagggccagc cttgcaaatt cccttttcgc     240
ttccagggta catcttatga ttcatgcaca acggaaggtc gcacagatgg ctaccgctgg     300
tgcggcacca cagaggatta tgaccgcgac aaaaaatacg gttttgtcc ggaaaccgca      360 ctgttcacca tgggtggtaa tgcggaagga caaccatgca gtttccatt ccgctttcag      420 ggaacctcat atgatagctg cacaacagag ggacgtacgg atggatacag atggtgcggt     480
acaaccgagg actacgatag agataagaaa tatggtttct gtcccgatca gggttatagc     540
ctg                                                                  543

<210> SEQ ID NO 27
<211> LENGTH: 181
<212> TYPE: PRT
<213> ORGANISM: Artificial Sequence
<220> FEATURE:
<223> OTHER INFORMATION: Exemplary peptide 333 comprising three modules
      corresponding to module 3 of the CBD of MMP-2

<400> SEQUENCE: 27

Glu Gly Gln Val Val Ser Thr Val Tyr Gly Asn Ser Glu Gly Ala Pro
1               5                   10                  15
Cys Val Phe Pro Phe Thr Phe Leu Gly Asn Lys Tyr Glu Ser Cys Thr
            20                  25                  30
Ser Ala Gly Arg Ser Asp Gly Phe Leu Trp Cys Ala Thr Thr Ala Asn
        35                  40                  45
Tyr Asp Asp Asp Arg Lys Trp Gly Phe Cys Pro His Glu Ala Leu Phe
    50                  55                  60
Thr Met Gly Gly Asn Ser Glu Gly Ala Pro Cys Val Phe Pro Phe Thr
65                  70                  75                  80
Phe Leu Gly Asn Lys Tyr Glu Ser Cys Thr Ser Ala Gly Arg Ser Asp
                85                  90                  95
Gly Lys Arg Trp Cys Ala Thr Thr Ala Asn Tyr Asp Asp Asp Arg Lys
            100                 105                 110
Trp Gly Phe Cys Pro Glu Thr Ala Met Ser Thr Val Gly Gly Asn Ser
        115                 120                 125
Glu Gly Ala Pro Cys Val Phe Pro Phe Thr Phe Leu Gly Asn Lys Tyr
    130                 135                 140
```

Glu Ser Cys Thr Ser Ala Gly Arg Ser Asp Gly Lys Met Trp Cys Ala
145                 150                 155                 160

Thr Thr Ala Asn Tyr Asp Asp Asp Arg Lys Trp Gly Phe Cys Pro Asp
                165                 170                 175

Gln Gly Tyr Ser Leu
            180

<210> SEQ ID NO 28
<211> LENGTH: 543
<212> TYPE: DNA
<213> ORGANISM: Artificial Sequence
<220> FEATURE:
<223> OTHER INFORMATION: DNA encoding exemplary peptide 333

<400> SEQUENCE: 28
gaaggtcagg ttgttagcac cgtttatggt aatagcgaag gtgcaccgtg tgttttccg      60
tttacctttc tgggtaacaa atatgaaagc tgtaccagcg caggtcgtag tgatggtttt   120
ctgtggtgtg caaccaccgc aaattatgat gatgatcgta atgggggttt ttgtccgcat   180
gaagcactgt ttaccatggg tggcaattct gaaggtgccc cttgcgtgtt tccttttaca   240
tttttaggca acaagtacga aagctgcacc tcagccggtc gttcagatgg taaacgttgg   300
tgcgccacca cagccaacta tgatgacgac agaaaatggg gcttctgtcc tgaaaccgca   360
atgagcaccg ttggtggcaa cagtgaaggc gctccatgcg ttttcccgtt cacattcctg   420
ggcaataaat acgaatcatg tacctctgca ggtcgctctg atggcaaaat gtggtgcgcg   480
acaacggcca attacgacga tgaccgcaag tggggctttt gcccagatca gggttatagc   540
ctg                                                                 543

<210> SEQ ID NO 29
<211> LENGTH: 4
<212> TYPE: PRT
<213> ORGANISM: Artificial Sequence
<220> FEATURE:
<223> OTHER INFORMATION: Linker sequence 1

<400> SEQUENCE: 29

Glu Gly Gln Val
1

<210> SEQ ID NO 30
<211> LENGTH: 58
<212> TYPE: PRT
<213> ORGANISM: Artificial Sequence
<220> FEATURE:
<223> OTHER INFORMATION: Amino acid sequence comprising a peptide
      comprising module 3 of CBD of MMP-9 with additional residues

<400> SEQUENCE: 30

Ser Thr Val Met Gly Gly Asn Ser Ala Gly Glu Leu Cys Val Phe Pro
1               5                   10                  15

Phe Thr Phe Leu Gly Lys Glu Tyr Ser Thr Cys Thr Ser Glu Gly Arg
                20                  25                  30

Gly Asp Gly Arg Leu Trp Cys Ala Thr Thr Ser Asn Phe Asp Ser Asp
            35                  40                  45

Lys Lys Trp Gly Phe Cys Pro Asp Gln Gly
        50                  55

<210> SEQ ID NO 31
<211> LENGTH: 176

```
<212> TYPE: PRT
<213> ORGANISM: Artificial Sequence
<220> FEATURE:
<223> OTHER INFORMATION: Amino acid sequence comprising CBD of MMP-9
      with additional residues

<400> SEQUENCE: 31

Pro Thr Arg Phe Gly Asn Ala Asp Gly Ala Ala Cys His Phe Pro Phe
1               5                   10                  15

Ile Phe Glu Gly Arg Ser Tyr Ser Ala Cys Thr Thr Asp Gly Arg Ser
            20                  25                  30

Asp Gly Leu Pro Trp Cys Ser Thr Thr Ala Asn Tyr Asp Thr Asp Asp
        35                  40                  45

Arg Phe Gly Phe Cys Pro Ser Glu Arg Leu Tyr Thr Gln Asp Gly Asn
    50                  55                  60

Ala Asp Gly Lys Pro Cys Gln Phe Pro Phe Ile Phe Gln Gly Gln Ser
65                  70                  75                  80

Tyr Ser Ala Cys Thr Thr Asp Gly Arg Ser Asp Gly Tyr Arg Trp Cys
                85                  90                  95

Ala Thr Thr Ala Asn Tyr Asp Arg Asp Lys Leu Phe Gly Phe Cys Pro
            100                 105                 110

Thr Arg Ala Asp Ser Thr Val Met Gly Gly Asn Ser Ala Gly Glu Leu
        115                 120                 125

Cys Val Phe Pro Phe Thr Phe Leu Gly Lys Glu Tyr Ser Thr Cys Thr
130                 135                 140

Ser Glu Gly Arg Gly Asp Gly Arg Leu Trp Cys Ala Thr Thr Ser Asn
145                 150                 155                 160

Phe Asp Ser Asp Lys Lys Trp Gly Phe Cys Pro Asp Gln Gly Tyr Ser
                165                 170                 175

<210> SEQ ID NO 32
<211> LENGTH: 6
<212> TYPE: PRT
<213> ORGANISM: Artificial Sequence
<220> FEATURE:
<223> OTHER INFORMATION: Linker sequence 4

<400> SEQUENCE: 32

Asp Gln Gly Tyr Ser Leu
1               5

<210> SEQ ID NO 33
<211> LENGTH: 707
<212> TYPE: PRT
<213> ORGANISM: Homo sapiens

<400> SEQUENCE: 33

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95
```

```
Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Thr Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510
```

```
Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
    530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705

<210> SEQ ID NO 34
<211> LENGTH: 49
<212> TYPE: PRT
<213> ORGANISM: Homo sapiens

<400> SEQUENCE: 34

Ala Asp Gly Ala Ala Cys His Phe Pro Phe Ile Phe Glu Gly Arg Ser
1               5                   10                  15

Tyr Ser Ala Cys Thr Thr Asp Gly Arg Ser Asp Gly Leu Pro Trp Cys
            20                  25                  30

Ser Thr Thr Ala Asn Tyr Asp Thr Asp Arg Phe Gly Phe Cys Pro
        35                  40                  45

Ser

<210> SEQ ID NO 35
<211> LENGTH: 60
<212> TYPE: PRT
<213> ORGANISM: Artificial Sequence
<220> FEATURE:
<223> OTHER INFORMATION: Amino acid sequence of a peptide comprising
      module 1 of CBD of MMP-9 with additional residues

<400> SEQUENCE: 35

Thr Arg Phe Gly Asn Ala Asp Gly Ala Ala Cys His Phe Pro Phe Ile
1               5                   10                  15
```

```
Phe Glu Gly Arg Ser Tyr Ser Ala Cys Thr Thr Asp Gly Arg Ser Asp
                20                  25                  30

Gly Leu Pro Trp Cys Ser Thr Ala Asn Tyr Asp Thr Asp Asp Arg
            35                  40                  45

Phe Gly Phe Cys Pro Ser Glu Arg Leu Tyr Thr Gln
        50                  55                  60

<210> SEQ ID NO 36
<211> LENGTH: 49
<212> TYPE: PRT
<213> ORGANISM: Homo sapiens

<400> SEQUENCE: 36

Ala Asp Gly Lys Pro Cys Gln Phe Pro Phe Ile Phe Gln Gly Gln Ser
1               5                   10                  15

Tyr Ser Ala Cys Thr Thr Asp Gly Arg Ser Asp Gly Tyr Arg Trp Cys
                20                  25                  30

Ala Thr Thr Ala Asn Tyr Asp Arg Asp Lys Leu Phe Gly Phe Cys Pro
            35                  40                  45

Thr

<210> SEQ ID NO 37
<211> LENGTH: 59
<212> TYPE: PRT
<213> ORGANISM: Artificial Sequence
<220> FEATURE:
<223> OTHER INFORMATION: Amino acid sequence of a peptide comprising
      module 2 of CBD of MMP-9 with additional residues

<400> SEQUENCE: 37

Arg Leu Tyr Thr Gln Asp Gly Asn Ala Asp Gly Lys Pro Cys Gln Phe
1               5                   10                  15

Pro Phe Ile Phe Gln Gly Gln Ser Tyr Ser Ala Cys Thr Thr Asp Gly
                20                  25                  30

Arg Ser Asp Gly Tyr Arg Trp Cys Ala Thr Thr Ala Asn Tyr Asp Arg
            35                  40                  45

Asp Lys Leu Phe Gly Phe Cys Pro Thr Arg Ala
        50                  55

<210> SEQ ID NO 38
<211> LENGTH: 49
<212> TYPE: PRT
<213> ORGANISM: Homo sapiens

<400> SEQUENCE: 38

Ser Ala Gly Glu Leu Cys Val Phe Pro Phe Thr Phe Leu Gly Lys Glu
1               5                   10                  15

Tyr Ser Thr Cys Thr Ser Glu Gly Arg Gly Asp Gly Arg Leu Trp Cys
                20                  25                  30

Ala Thr Thr Ser Asn Phe Asp Ser Asp Lys Lys Trp Gly Phe Cys Pro
            35                  40                  45

Asp
```

The invention claimed is:

1. A peptide comprising a plurality of modules corresponding to module 1 of the collagen binding domain of MMP-2, a plurality of modules corresponding to module 2 of the collagen binding domain of MMP-2, or a plurality of modules corresponding to module 3 of the collagen binding domain of MMP-2, wherein module 1 comprises the amino acid sequence set out in SEQ ID NO: 6 or a sequence with at least 90% sequence identity thereto, wherein module 2 comprises the amino acid sequence set out in SEQ ID NO: 11 or a sequence with at least 90% sequence identity thereto, and wherein module 3 comprises the amino acid sequence set out in SEQ ID NO: 17 or a sequence with at least 90% sequence identity thereto.

2. A peptide according to claim 1, comprising a plurality of modules corresponding to module 2 of the collagen binding domain of MMP-2, wherein module 2 comprises the amino acid sequence set out in SEQ ID NO: 11 or a sequence with at least 90% sequence identity thereto.

3. A peptide according to claim 1, comprising a total of three modules corresponding to module 2 of the collagen binding domain of MMP-2.

4. A peptide according to claim 1, comprising a plurality of modules corresponding to module 1 of the collagen binding domain of MMP-2, wherein module 1 comprises the amino acid sequence set out in SEQ ID NO: 6 or a sequence with at least 90% sequence identity thereto.

5. A peptide according to claim 1, comprising at least one linker sequence flanking at least one module of the collagen binding domain of MMP-2.

6. A peptide according to claim 5, wherein the at least one linker sequence is selected from the group consisting of: SEQ ID NO: 29, SEQ ID NO: 32, linker sequence 2 consisting of amino acid residues HEA, and linker sequence 3 consisting of amino acid residues ETA.

7. A peptide according to claim 6, comprising all of said linker sequences.

8. A peptide according to claim 1, comprising a variant of module 2 of the collagen binding domain of MMP-2 having the amino acid sequence set out in SEQ ID NO: 14.

9. A peptide according to claim 1, comprising a variant of module 2 of the collagen binding domain of MMP-2 wherein the variant has
 at least one amino acid corresponding to residues 19 or 51 of SEQ ID NO: 14 is modified as compared to the corresponding residue of SEQ ID NO: 14.

10. A peptide according to claim 9 comprising a plurality of modules corresponding to module 2 of the collagen binding domain of MMP-2, comprising a sequence set out in SEQ ID NO: 13, or comprising a plurality of modules corresponding to module 2 of the collagen binding domain of MMP-2, comprising a sequence set out in SEQ ID NO: 14, or both.

11. A peptide according claim 1, wherein the peptide has a binding affinity for type II collagen gelatin that is at least 10-fold higher than the binding affinity of the native CBD of MMP-2.

12. A peptide according to claim 1, comprising the amino acid sequence set out in SEQ ID NO: 25.

13. A peptide according to claim 12, consisting of the amino acid sequence set out in SEQ ID NO: 25.

14. A conjugate comprising a targeting peptide and a payload, wherein the targeting peptide comprises a plurality of module 1 of the collagen binding domain of MMP-2, a plurality of module 2 of the collagen binding domain of MMP-2, or a plurality of module 3 of the collagen binding domain of a MMP-2, wherein module 1 comprises the amino acid sequence set out in SEQ ID NO: 6 or a sequence with at least 90% sequence identity thereto, wherein module 2 comprises the amino acid sequence set out in SEQ ID NO: 11 or a sequence with at least 90% sequence identity thereto, and wherein module 3 comprises the amino acid sequence set out in SEQ ID NO: 17 or a sequence with at least 90% sequence identity thereto.

15. A conjugate according to claim 14, wherein the targeting peptide comprises the amino acid sequence of SEQ ID NO: 25.

16. A conjugate according to claim 14, wherein the payload comprises a therapeutic payload and the conjugate is a therapeutic conjugate.

17. A therapeutic conjugate according to claim 16, wherein the therapeutic payload is selected from the group consisting of: a therapeutic cell; a therapeutic drug molecule; and a therapeutic growth factor.

18. A conjugate according to claim 14, wherein the payload comprises a non-therapeutic payload, and the conjugate is a non-therapeutic conjugate.

19. A non-therapeutic conjugate according to claim 18, wherein the payload comprises an imaging agent.

20. A method of treating a disorder associated with generation or accumulation of gelatin, comprising administering a peptide according to claim 1, or conjugate comprising a peptide according to claim 1 and a payload.

\* \* \* \* \*